(12) United States Patent
Carriero et al.

(10) Patent No.: US 8,354,374 B2
(45) Date of Patent: Jan. 15, 2013

(54) PEPTIDES HAVING PHARMACOLOGICAL ACTIVITY FOR TREATING DISORDERS ASSOCIATED WITH ALTERED CELL MIGRATION, SUCH AS CANCER

(75) Inventors: Maria Vincenza Carriero, Naples (IT); Mario De Rosa, Naples (IT); Vincenzo Pavone, Naples (IT)

(73) Assignee: Pharmaphelix S.R.L., Cercola (Napoli) (IT)

( * ) Notice: Subject to any disclaimer, the term of this patent is extended or adjusted under 35 U.S.C. 154(b) by 759 days.

(21) Appl. No.: 12/376,465

(22) PCT Filed: Jul. 19, 2007

(86) PCT No.: PCT/EP2007/006424
§ 371 (c)(1),
(2), (4) Date: Feb. 24, 2009

(87) PCT Pub. No.: WO2008/017372
PCT Pub. Date: Feb. 14, 2008

(65) Prior Publication Data
US 2011/0230397 A1    Sep. 22, 2011

(30) Foreign Application Priority Data
Aug. 9, 2006  (IT) .............................. MI2006A1607

(51) Int. Cl.
*A61K 38/07*    (2006.01)
*A61K 38/08*    (2006.01)
*C07K 5/11*     (2006.01)
*C07K 7/06*     (2006.01)

(52) U.S. Cl. ...... 514/4.2; 514/13.3; 514/16.6; 514/18.7; 514/19.3; 514/19.8; 514/20.8; 514/21.8; 514/21.9; 530/330

(58) Field of Classification Search ........................ None
See application file for complete search history.

(56) References Cited

U.S. PATENT DOCUMENTS

| 6,046,167 | A | 4/2000 | Balasubramaniam |
| 6,815,426 | B2 * | 11/2004 | Scialdone et al. ............. 514/1.9 |
| 2003/0009022 | A1 | 1/2003 | Klein et al. |
| 2003/0166568 | A1 * | 9/2003 | Kricek et al. .................. 514/14 |

FOREIGN PATENT DOCUMENTS

| GB | 2097404 A | * 11/1982 |
| WO | 00/11022 A | 3/2000 |
| WO | 02/23184 A | 3/2002 |
| WO | 02/058714 A | 8/2002 |
| WO | 03/064447 A | 8/2003 |
| WO | 2004/085455 A | 10/2004 |
| WO | 2006/038208 A | 4/2006 |

OTHER PUBLICATIONS

Ly et al. Cationic peptides containing tyrosine protect against radiation-induced oxidative DNA damage. Int. J. Radiat. Biol. Jun. 2006, vol. 82, No. 6, pp. 421-433.*

Fazioli, et al., A urokinase-sensitive region of the human urokinase receptor is responsible for its chemotactic activity, EMBO Journal, 1997, 16(24), pp. 7279-7286.

Karlsson, et al., The peptide Trp-Lys-Tyr-Met-Val-D-Met activates neutrophils through the formyl peptide receptor only when signaling through the formylpeptde receptor like 1 is blocked, Biochemical pharmacology, 2006, vol. 71(10), pp. 1488-1496.

Le, et al., Pleiotropic roles of formyl peptide receptors, Cytokine & growth factor reviews, 2001, vol. 12(1), pp. 91-105.

* cited by examiner

*Primary Examiner* — Jeffrey E Russel
(74) *Attorney, Agent, or Firm* — Lucas & Mercanti, LLP

(57) ABSTRACT

Peptides and their functionally equivalent derivatives, in salt form or non-salt form, effective in the treatment and prevention of tumor, with the general formula $L_1$-$X_1$-$X_2$-$X_3$-$X_4$, wherein: $L_1$ is H, or acyl, or any natural or non-natural amino acid; $X_2$ is any natural or non-natural amino acid, optionally N-alkylated and/or Cα-alkylated; $X_4$ is any natural or non-natural hydrophobic amino acid, optionally Cα-alkylated and/or amidated at the C-terminal end, or any hydrophobic amino alcohol, or a hydrophobic gem-diamine, optionally N'-alkylated or N'-acylated.

14 Claims, No Drawings

PEPTIDES HAVING PHARMACOLOGICAL ACTIVITY FOR TREATING DISORDERS ASSOCIATED WITH ALTERED CELL MIGRATION, SUCH AS CANCER

This invention relates to linear peptides and their functionally equivalent derivatives, whether "in salt form or non-salt form", containing four or five amino acid residues, at least one of which is hydrophobic and at least two of which are basic, hereinafter called "PICM" (Peptide Inhibitors of Cell Motility" and the pharmaceutical compositions containing them as active ingredients. The compounds according to the invention are effective in the treatment and prevention of tumors, especially those which are highly invasive and/or liable to metastasize, and in the treatment of disorders connected with neo-angiogenesis and neo-vascularization, and those associated with altered cell motility such as autoimmune disease and chronic inflammatory disorders like rheumatoid arthritis and psoriasis, chronic granulomatous disorders, retinopathies, macular degeneration, and oedema, Kaposi's sarcoma and diseases associated with herpes virus infection.

BACKGROUND OF THE INVENTION

Current tumour treatments are limited by the existence of highly malignant cell types, which intrinsically fail to respond to conventional treatments (gliomas, sarcomas, etc.), or by the onset of selective advantages, which promote the selection and consequent proliferation of resistant tumour clones during treatment (Woodhouse, E. C., et al., Cancer 80:1529-1537, 1997). Conventional treatments are mainly designed to inhibit the growth of the tumour rather than preventing its metastatic spread, which is still the main cause of treatment failures (Shevde L A et al. Cancer Lett, 198:1-20, 2003).

The general characteristic of current tumour treatments is the use of highly cytotoxic compounds which, although they act selectively on malignant cells, inevitably have devastating systemic effects on the body. The result is that current treatments generally involve very high social, human and financial costs.

This overall picture demonstrates that: a) there is a pressing need to develop effective treatments for currently untreatable tumours; b) there is a strong need to reduce the side effects which make patients' quality of life unacceptable when they are treated with current anti-tumour drugs, and can even cause death in debilitated patients; c) the efficacy of treatments needs to be improved by using drugs that interfere both with the growth process and with the metastatic spread of the tumour; d) the cost of tumour treatments needs to be made more acceptable.

It was recently reported that the numerous biological actions of the peptide Metastin, of human and murine derivation (WO 00/24890, WO 01/75104, WO 02/85399) include an effect in the prevention or treatment of cancer. WO 06/001499, which relates to Metastin and its derivatives, claims a very broad series of compounds, estimated at over $10^{10}$ different structures, containing 4 to 54 amino acid residues, natural and non-natural, for which a very wide variety of biological activity is reported, such as inhibition of metastatic spread and growth of tumours, control of the pancreatic function and prevention of acute and chronic pancreatitis, control of the placental function and use in the treatment of foetal hypoplasia, abnormal glucose metabolism, abnormalities in the lipid metabolism, infertility, endometriosis, premature puberty, Alzheimer's disease, disorders affecting the cognitive sphere, obesity, hyperlipidaemia, diabetes mellitus type II, hyperglycaemia, hypertension, diabetic neuropathies, diabetic nephropathies, diabetic retinopathies, oedema, urinary disorders, insulin resistance, unstable diabetes, fatty atrophy, insulin allergies, atherosclerosis, thrombotic disorders, lipotoxicity, and use in treatments to improve the function of the gonads and stimulate ovulation. The simultaneous existence of such different biological actions for each of these compounds certainly represents a major limitation, not an advantage, with a view to the therapeutic application of this class of molecules. This wide variety of biological functions is closely associated with the interaction of Metastin and its derivatives with the specific cell receptor GPR54, also known as Kiss-1R, Kisspeptins receptor, Metastin receptor, hypogonadotropin 1 or hOT7T175 (Ohtaki T., et al., Nature 411:613-617, 2001; Clements M. K., et al., Biochem. Biophys. Res. Commun. 284:1189-1193, 2001; Muir A. I., et al., J. Biol. Chem. 276:28969-28975; 2001; Kotani M., et al., J. Biol. Chem. 276:34631-34636, 2001; Seminara S. B., et al., N. Engl. J. Med. 349:1614-1627, 2003; Grimwood J., et al., Nature 428:529-535, 2004; Colledge W. H., Trends Endocrinol. Metab. 15:448-453, 2004; Hori A., et al., Biochem. Biophys. Res. Commun. 286:958-963, 2001; Janneau J.-L., et al., J. Clin. Endocrinol. Metab. 87:5336-5339, 2002; Ringel M. D., et al., J. Clin. Endocrinol. Metab. 87:2399-2399, 2002; de Roux N., et al., Proc. Natl. Acad. Sci. U.S.A. 100:10972-10976, 2003; Ikeguchi M., et al., J. Cancer Res. Clin. Oncol. 129:531-535, 2003; Ikeguchi M., et al., Clin. Cancer Res. 10:1379-1383, 2004; Bilban M., et al., J. Cell Sci. 117:1319-1328, 2004; Becker J. A. J., et al., Biochem. Biophys. Res. Commun. 326:677-686, 2005; Semple R. K., et al., J. Clin. Endocrinol. Metab. 90:1849-1855, 2005).

As regards the anti-tumoral activity of Metastin and its derivatives, WO 06/001499 reports a modest activity, limited to experimental animal models, at the dose of 70-140 µg/kg, which reduces the tumour mass by not more than 20%. It has also been demonstrated that long-term administration of Kisspeptin-54, one of the analogues of Metastin, causes the adverse effect of atrophy of the gonads in the rat (E. L. Thomson et al., Am. J. Physiol. Endocrinol. Metab. 291, 1074-1082, 2006).

DESCRIPTION OF THE INVENTION

This invention concerns tetra-peptides and penta-peptides and their functionally equivalent derivatives, in salt form or non-salt form, containing at least two basic and at least one hydrophobic amino acids (hereinafter indicated by the code PICM), which inhibit cell migration in vitro at a M concentrations ($10^{-8}$ M), and have a powerful antitumoral action in vivo, reducing the tumor mass from 30 to 70% at the dose as low as 15 µg/Kg. They are effective in all disorders associated with neo-angiogenesis and neo-vascularisation, and do not present any acute or sub-acute toxicity up to doses approx. 1000 times higher than the therapeutic dose.

Unlike Metastin and its derivatives, the activity of the peptides according to the invention is not correlated with cell receptor GPR54, but is strictly correlated with their specific interaction with the FPR cell receptors.

Some FPR receptor antagonists are known (Edwards et al. Mol Pharmacol. 68:1301-10, 2005; Karlsson et al. Biochem Pharmacol. 71:1488-96, 2006), all of which are chemically distinct from the PICMs.

The PICMs therefore represent a new class of active constituents which possess biological and pharmacological activities that are far more potent than and different from those of Metastin and its derivatives and the FPR receptor antagonists.

In clinical practice, PICMs are effective against a large number of tumours, act at low doses, and do not present any systemic toxicity or adverse effects.

The PICMs are also effective in the treatment of disorders connected with neo-angiogenesis and neo-vascularisation, and those associated with altered cell motility such as autoimmune diseases and chronic inflammatory disorders like rheumatoid arthritis and psoriasis, chronic granulomatous disorders, retinopathies, macular degeneration and oedema, Kaposi's sarcoma and diseases associated with herpes virus infection.

DETAILED DESCRIPTION OF THE INVENTION

The peptides according to the invention and their functionally equivalent derivatives, in salified or non-salified form, have the general formula $L_1$-$X_1$—$X_2$—$X_3$—$X_4$, wherein: $L_1$ is H, or acyl, or any natural or non-natural amino acid, optionally N-acylated or N-alkylated and/or Cα-alkylated; preferably, $L_1$ is H, or acyl, or Glu, Gln, optionally N-acylated or N-alkylated and/or Cα-alkylated, Pro, hydroxy-Pro, thio-Pro, Azt, Pip, pGlu, optionally N-acylated and/or Cα-alkylated, Aib, Ac3c, Ac4c, Ac5c, Ac6c, optionally N-acylated or N-alkylated; even more preferably $L_1$ is H or acyl, Aib, Ac3c, Ac4c, Ac5c or Ac6c, optionally N-acylated or N-alkylated;
$X_1$ and $X_3$, which are equal or different, are any natural or non-natural basic amino acid, optionally N-alkylated and/or Cα-alkylated; preferably, $X_1$ and $X_3$, which are equal or different, optionally N-alkylated and/or Cα-alkylated, are chosen from among Arg, Orn, Lys, optionally guadinylated, and phenylalanine substituted in the meta or para positions with an amine or guanidine group;
$X_2$ is any natural or non-natural amino acid, optionally N-alkylated and/or Cα-alkylated, with the proviso that it is not glycine and amino acids mono-substituted on the α carbon atom with a linear or cyclic alkyl group, from 1 to 10 carbon atoms, or of amino acids mono substituted on the α carbon atom with a linear or cyclic alkyl group containing 4 to 10 carbon atoms, or amino acids mono-substituted on the α carbon atom with an alkyl group containing 1 to 8 carbon atoms, optionally substituted with a carbamoyl, hydroxyl or aromatic group; $X_2$ is preferably chosen from among Glu, Lys, optionally N-alkylated and/or Cα-alkylated, Aib, Ac3c, Ac4c, Ac5c, and Ac6c, optionally N-alkylated; more preferably, $X_2$ is chosen from among Aib, Ac3c, Ac4c, Ac5c and Ac6c, optionally N-alkylated;
$X_4$ is any hydrophobic amino acid, optionally Cα-alkylated and/or amidated at the C-terminal end, or any hydrophobic amino alcohol or any hydrophobic gem-diamine, optionally N'-alkylated or N'-acylated; $X_4$ is preferably chosen from among Phe, h-Phe, Tyr, Trp, 1-NaI, 2-NaI, h-1-NaI, h-2-NaI, Cha, Chg and Phg, optionally Cα-alkylated and/or amidated at the C-terminal end.

"Natural amino acids" refers to the amino acids constituting the protein of living organisms.

"Non-natural amino acids" refers to: α-amino acids in the D series or β-amino acids; dehydro-amino acids; amino acids di-substituted on the α carbon atom with alkyl or aryl groups containing up to 11 carbon atoms; natural amino acids, as defined above, containing, on the side chain, hydroxy, amino or thio groups functionalised with alkyls, acyls, aryls or acylaryls containing 1 to 11 carbon atoms; natural amino acids, as defined above, containing, on the side chain, carboxy groups functionalised with primary or secondary amines or aliphatic or aromatic alcohols containing up to 11 carbon atoms; cyclic amino acids such as Azt, thio-Pro, Ac3c, Ac4c, Ac5c, Ac6c, and pGlu acid; homo-amino acids; amino acids substituted by cycloalkyl or aryl groups such as β-1-naphthyl-alanine, β-2-naphthyl-alanine, homo-β-1-naphthyl-alanine, homo-β-2-naphthyl-alanine, cyclohexyl-alanine, cyclohexyl-glycine, and phenyl-glycine. Other non-natural amino acids are those reported in: "Diversity of synthetic peptides", Konishi et al. First International Peptide Symposium, Kyoto, Japan, 1997.

The term "any basic amino acid" refers to any natural or non-natural amino acid as defined above, containing at least one imidazole, amino, guanidino, pyridinium or urea group in the side chain.

The term "any hydrophobic amino acid" refers to α-, β- and dehydro-amino acids in the series: Leu, n-Leu, Ile, allo-Ile, Val, n-Val, Phe, h-Phe, Tyr, Trp, 1-NaI, 2-NaI, h-1-NaI, h-2-NaI, Cha, Chg and Phg; natural and non-natural amino acids as defined above, containing on the side chain hydroxy, amino or thio groups functionalised with alkyls, acyls, aryls or acylaryls containing 1 to 11 carbon atoms; natural and non-natural amino acids, as defined above, containing on the side chain carboxy groups functionalised with primary or secondary amines or aliphatic or aromatic alcohols containing up to 11 carbon atoms; phenylalanines mono- and di-substituted in the ortho, meta and para positions of the aromatic ring with halogens or with alkyl, O-alkyl or S-alkyl groups; β-2- and β-3-thienylalanine, β-2- and β-3-furanyla-lanine; derivatives of 2,3 di-amino propionic acid and 2,4 di-amino butyric acid functionalised with alkyls, acyls, aryls or acylaryls containing up to 11 carbon atoms.

The term "any hydrophobic amino alcohol" refers to "any hydrophobic amino acid" as defined above, wherein the carboxyl function is substituted with an OH group.

The term "any hydrophobic gem-diamine" refers to "any hydrophobic amino acid" as defined above, wherein the carboxyl function is substituted with an $NH_2$ group.

The term "acyl" means an acyl group containing 1 to 9 carbon atoms.

The term "N-acylated" means the introduction of an acyl, as defined above, onto the terminal amino nitrogen.

The term "N-alkylated" means the introduction of an alkyl residue containing 1 to 9 carbon atoms onto the amide nitrogen.

The term "amidated" means the amidation of the C-terminal carboxyl with a primary or secondary amine containing a total of 0 to 14 carbon atoms.

The term "Cα-alkylated" means the introduction onto the α carbon atom of an alkyl residue containing 1 to 9 carbon atoms.

The term "functionally equivalent derivatives" means derivatives of the compounds with general formula I characterised by structural modifications conventionally used in peptide chemistry to modulate their pharmacodynamic or pharmacokinetic properties. These include pseudo-peptides wherein one or more peptide bonds are substituted by —$CH_2$—NH— (Guichard G, et al., *J Biol Chem.;* 270:26057-9 1995), derivatives with one or more inverted peptide bonds (Carotti A., et al. *Biopolymers* 60, 322-332, 2001; Chorev, M., et al. *Science* 204, 1210-1212 1979; Pallai, P., et al. *Biochemistry* 24, 1933-1941. 1985; Rodriguez M. E. et al. *J. Med. Chem.* 30, 758-763 1987), β-peptide derivatives (Horne W. S. et al. *J. Am. Chem. Soc.* 129 4178-4180 2007), wherein one or more peptide bonds are formed by at least one β-amino acid, and derivatives containing one or more dehydro-amino acids (Busetti V. et al. *Int. J. Biol. Macromol.* 14, 23-28 1992). Derivatives with elongation of the chain from the N-terminal side are also functionally equivalent derivatives.

The following are the conventional abbreviations used for some of the non-natural amino acids which can be included in the formulas of the peptides according to the invention:
Azt=azetidinic acid, Pip=pipecolic acid, Aib=α-amino-isobutyric acid, Ac3c=1-aminocyclopropan-1-carboxylic acid, Ac4c=1-aminocyclobutan-1-carboxylic acid, Ac5c=1-aminocyclopentan-1-carboxylic acid, Ac6c=1-aminocyclohexan-1-carboxylic acid, Abu=α-amino-n-butyric acid, n-Leu=norleucine, n-Val=norvaline, h-Phe=homo-phenylalanine, 1-NaI=β-1-naphthyl-alanine, 2-NaI=β-2-naphthyl-alanine, h-1-NaI=homo-β-1-naphthyl-alanine, h-2-NaI=homo-β-2-naphthyl-alanine, Cha=cyclohexyl-alanine, Chg=cyclohexyl-glycine, Phg=phenyl-glycine, pGlu=pyroglutamic acid, Dap=2,3 di-amino-propionic acid, Dab=2,4 diaminobutyric acid, N(Me)Arg=N-methyl-arginine, α(Me)Phe=C-alpha-methyl-phenylalanine.

Preferably, L1 is acetyl, Glu, pGlu, acetyl-Aib, X1 is Arg or N(Me)Arg, X2 is Glu, Aib, Ac5c, X3 is Arg, N(Me)Arg, and X4 is Phe-NH$_2$, Tyr-NH$_2$, Trp-NH$_2$, α(Me)Phe-NH$_2$, Phe-OH, Tyr-OH, Trp-OH. The particularly preferred peptides according to the invention are chosen from among: Ac-Arg-Glu-Arg-Phe-NH$_2$ SEQ ID NO. 66; Ac-Arg-Glu-N(Me)Arg-Phe-NH$_2$ SEQ ID NO. 4; Ac-Arg-Aib-Arg-Phe-NH$_2$ SEQ ID NO. 13; Ac-Arg-Aib-N (Me)Arg-Phe-NH$_2$ SEQ ID NO. 17; Ac-Arg-Ac5c-Arg-Phe-NH$_2$ SEQ ID NO. 26; Ac-Arg-Ac5c-N(Me)Arg-Phe-NH$_2$ SEQ ID NO. 29; Ac-N(Me)Arg-Aib-Arg-Phe-NH$_2$ SEQ ID NO. 52; Ac-N(Me)Arg-Aib-N(Me)Arg-Phe-NH$_2$ SEQ ID NO. 53; Ac-Arg-Aib-N(Me)Arg-Phe-NH$_2$ SEQ ID NO. 54; Ac-Arg-Aib-Arg; α(Me)Phe-NH$_2$; Ac-N(Me)Arg-Aib-Arg-α(Me)Phe-NH$_2$ SEQ ID NO. 56; Ac-N(Me)Arg-Aib-N(Me)Arg-α(Me)Phe-NH$_2$ SEQ ID NO. 57; Ac-Arg-Aib-N(Me)Arg-α(Me)Phe-NH$_2$ SEQ ID NO. 58;

The peptides according to the invention can be synthesised with the various techniques reported in the literature; see, for example, Schroeder et al. "The Peptides" vol 1, Academic Press, 1965; Bodanszky et al. "Peptide Synthesis Interscience Publisher, 1966; Barany & Merrifield, "The peptides; Analysis, Synthesis, Biology", 2, Chapter 1, Academic Press, 1980. These techniques include solid-phase peptide synthesis, peptide synthesis in solution, organic chemistry synthesis methods, or any combination thereof. The synthesis method chosen will obviously depend on the composition of the particular peptide. Preferably, the methods used will be based on appropriate combinations of solid-phase techniques and classic methods in solution, which involve low manufacturing costs, especially on an industrial scale. In detail, these methods involve: i) synthesis in solution of fragments of the peptide chain through successive coupling of suitably activated N-protected amino acids to an amino acid or a C-protected peptide chain, with isolation of the intermediates, subsequent selective deprotection of the N and C-terminal ends of said fragments and, where necessary, of the side chains, until the desired peptide is obtained; ii) solid-phase synthesis of the peptide chain from the C-terminal to the N-terminal end on an insoluble polymer medium. The peptide is removed from the resin by hydrolysis with anhydrous hydrofluoric acid or trifluoroacetic acid in the presence of suitable scavengers.

The peptides according to the invention are active on many types of human and animal tumours, preventing their growth and metastatic spread.

The compounds according to the invention are advantageous, especially compared with Metastin and the correlated peptides reported in WO 06/001499, in terms of anti-tumoral effect and effective doses. The peptides according to the invention induce a far more effective response in reducing tumours (20% reduction by Metastin derivatives, 70% reduction by the products according to the invention), at lower concentrations.

For the proposed therapeutic uses, the peptides according to the invention can be formulated as such, or in the form of salts, in pharmaceutical compositions for oral, parenteral, topical, spray or transdermal administration, possibly in association with other active ingredients. The unit doses in humans can vary within a wide range, typically from 0.1 µg to 1 g per dose, and preferably between 0.1 mg and 100 mg, which can easily be determined by one skilled in the art according to the disorder to be treated, its severity, and the weight, sex and age of the patient.

The following examples illustrate the invention in greater detail.

EXAMPLE 1

Preparation of PICM1, a compound with formula 1 wherein: L1 is Ace, $X_1$ and $X_3$ are Arg, $X_2$ is Glu, and $X_4$ is Phe-NH$_2$. The % formula of PICM1 is therefore Ac-Arg-Glu-Arg-Phe-NH$_2$ SEQ ID NO. 66.

An automatic peptide synthesiser starting with 2.5 g of Rink-amide resin (0.2 meq/g) equal to 0.5 mmol of amine groups is used for the synthesis. The Fmoc group is hydrolysed in two successive phases with 30% piperidine in DMF for 3 min. and 7 min. The following compounds are then reacted, in the order listed: Fmoc-Phe-OH (0.581 g), Fmoc-Arg(Pbf)-OH (0.974 g), Fmoc-Glu(OtBu)-OH (0.638 g), Fmoc-Arg (Pbf)-OH (0.974 g) and acetic acid (0.090 g).

The duration of the acylations is 1 h; the resin is then washed and the reaction tested with the Kaiser ninhydrin assay. If the response is negative, the Fmoc group is hydrolysed as described above before the next amino acid is coupled. All the amino acids are coupled by dissolving 1.5 mmol of amino acid in 4 ml of DMF, and added to the deprotected resin with a mixture of activators consisting of a solution of 0.780 g of PyBop in 2 ml of DMF, 0.230 g of HOBT in 2 ml of DMF, and 250 ml of DIEA. For the detachment of the peptide from the resin and the concomitant deprotection of the side chains, the dry resin is placed in a reactor to which 20 ml of a solution of TFA, thioanisole, mercaptoethanol and anisole, in the ratio of 9:0.5:0.3:0.2 in weight, is added. The reaction mixture is kept under agitation for 2 h. The filtrate is reduced to a small volume and the peptide is extracted by precipitation with ether. The precipitate is dissolved with water and freeze-dried. Finally, the peptide is purified by reverse-phase chromatography and characterised by analytical HPLC, using a Vydac C18 0.46×25 cm column eluted with a linear gradient in acetonitrile containing 0.1% (v/v) of trifluoroacetic acid (phase B) against 0.1% (v/v) aqueous trifluoroacetic acid (Phase A), from 5 to 70% in B in 35 min at a flow rate of 1 ml/min, with UV detection at 210 nm. Retention time (Rt)=11.8 min.; chromatographic purity >99%. FAB-MS: (MH)$^+$=650.

EXAMPLE 2

Preparation of PICM2, a compound with formula I wherein L1 is pGlu, $X_i$ and $X_3$ are Arg, $X_2$ is Glu and $X_4$ is Tyr. The % formula of PICM2 is therefore pGlu-Arg-Glu-Arg-Tyr-OH SEQ ID NO. 67.

An automatic peptide synthesiser starting with 2.5 g of Fmoc-Tyr(tBu)-Novasyn-TGA resin (0.2 meq/g), equal to 0.5 mmol of amine groups, is used for the synthesis. The Fmoc group is hydrolysed in two successive phases with 30% piperidine in DMF for 3 min and 7 min. The following amino acids are then reacted in the order listed: Fmoc-Arg(Pbf)-OH (0.974 g), Fmoc-Glu(OtBu)-OH (0.638 g), Fmoc-Arg(Pbf)-OH (0.974 g) and Fmoc-pGlu-OH (0.638 g).

The duration of the acylations is 1 h; the resin is then washed and the reaction tested with the Kaiser ninhydrin assay. If the response is negative, the Fmoc group is hydrolysed as described above before the next amino acid is coupled. All the amino acids are coupled by dissolving 1.5 mmol of amino acid in 4 ml of DMF and added to the deprotected resin with a mixture of activators consisting of a solution of 0.780 g of PyBop in 2 ml of DMF, 0.230 g of HOBT in 2 ml of DMF, and 250 ml of DIEA. For the detachment of the peptide from the resin and the concomitant deprotection of the side chains, the dry resin is placed in a reactor to which 20 ml of a solution of TFA, thioanisole, mercaptoethanol and anisole, in the ratio of 9:0.5:0.3:0.2 in weight, is added. The reaction mixture is kept under agitation for 2 h. The filtrate is reduced to a small volume and the peptide is extracted by precipitation with ether. The precipitate is dissolved with water and freeze-dried. Finally, the peptide is purified by reverse-phase chromatography and characterised by analytical HPLC, using a Vydac C18 0.46×25 cm column eluted with a linear gradient in acetonitrile containing 0.1% (v/v) trifluoroacetic acid (phase B) against 0.1% (v/v) aqueous trifluoroacetic acid (Phase A), from 5 to 70% in B in 35 min at a flow rate of 1 ml/min, with UV detection at 210 nm. Retention time (Rt)=12.8 min; chromatographic purity >99%. FAB-MS: $(MH)^+$=589.

EXAMPLE 3

Sequences and characterisation data of peptides synthesised with the methods described in examples 1 and 2.

Table 1 shows the sequences and characterisation data of a series of peptides synthesised with the methods described in example 1, consisting of PICM3 to PICM39 and PICM54 to PICM67, and in example 2, consisting of PICM40 to PICM53, suitably adapted to the specific sequences according to the common peptide synthesis methodologies.

TABLE 1

Examples of the peptide sequences according to the invention and their characterisation

| Name | L1 | X1 | X2 | X3 | X4 | Rt (min) | MH+ | SEQ ID NO. |
|---|---|---|---|---|---|---|---|---|
| PICM3 | Glu | Arg | Glu | Arg | Phe-$NH_2$ | 12.6 | 736 | SEQ ID NO. 1 |
| PICM4 | Ac | Arg | Glu | Arg | Tyr-$NH_2$ | 13.1 | 666 | SEQ ID NO. 2 |
| PICM5 | Ac | Arg | Glu | Arg | Trp-$NH_2$ | 14.3 | 689 | SEQ ID NO. 3 |
| PICM6 | Ac | Arg | Glu | N(Me)Arg | Phe-$NH_2$ | 12.9 | 664 | SEQ ID NO. 4 |
| PICM7 | Ac | Arg | Glu | N(Me)Arg | Tyr-$NH_2$ | 13.4 | 680 | SEQ ID NO. 5 |
| PICM8 | Ac | Arg | Glu | N(Me)Arg | Trp-$NH_2$ | 14.6 | 703 | SEQ ID NO. 6 |
| PICM9 | pGlu | Arg | Glu | N(Me)Arg | Phe-$NH_2$ | 12.7 | 732 | SEQ ID NO. 7 |
| PICM10 | pGlu | Arg | Glu | N(Me)Arg | Tyr-$NH_2$ | 13.2 | 748 | SEQ ID NO. 8 |
| PICM11 | pGlu | Arg | Glu | N(Me)Arg | Trp-$NH_2$ | 14.4 | 771 | SEQ ID NO. 9 |
| PICM12 | pGlu | Arg | Glu | Arg | Phe-$NH_2$ | 12.4 | 718 | SEQ ID NO. 10 |
| PICM13 | pGlu | Arg | Glu | Arg | Tyr-$NH_2$ | 12.8 | 734 | SEQ ID NO. 11 |
| PICM14 | pGlu | Arg | Glu | Arg | Trp-$NH_2$ | 14.0 | 757 | SEQ ID NO. 12 |
| PICM15 | Ac | Arg | Aib | Arg | Phe-$NH_2$ | 15.5 | 606 | SEQ ID NO. 13 |
| PICM16 | Ac | Arg | Aib | Arg | Tyr-$NH_2$ | 15.2 | 622 | SEQ ID NO. 14 |
| PICM17 | Ac | Arg | Aib | Arg | Trp-$NH_2$ | 16.4 | 645 | SEQ ID NO. 15 |
| PICM18 | Ac-Aib | Arg | Aib | Arg | Phe-$NH_2$ | 17.3 | 694 | SEQ ID NO. 16 |
| PICM19 | Ac | Arg | Aib | N(Me)Arg | Phe-$NH_2$ | 18.3 | 620 | SEQ ID NO. 17 |
| PICM20 | Ac | Arg | Aib | N(Me)Arg | Tyr-$NH_2$ | 18.1 | 636 | SEQ ID NO. 18 |
| PICM21 | Ac | Arg | Aib | N(Me)Arg | Trp-$NH_2$ | 19.3 | 659 | SEQ ID NO. 19 |
| PICM22 | pGlu | Arg | Aib | N(Me)Arg | Phe-$NH_2$ | 14.5 | 688 | SEQ ID NO. 20 |
| PICM23 | pGlu | Arg | Aib | N(Me)Arg | Tyr-$NH_2$ | 14.2 | 704 | SEQ ID NO. 21 |
| PICM24 | pGlu | Arg | Aib | N(Me)Arg | Trp-$NH_2$ | 16.0 | 727 | SEQ ID NO. 22 |
| PICM25 | pGlu | Arg | Aib | Arg | Phe-$NH_2$ | 15.4 | 674 | SEQ ID NO. 23 |
| PICM26 | pGlu | Arg | Aib | Arg | Tyr-$NH_2$ | 15.2 | 690 | SEQ ID NO. 24 |
| PICM27 | pGlu | Arg | Aib | Arg | Trp-$NH_2$ | 16.6 | 713 | SEQ ID NO. 25 |
| PICM28 | Ac | Arg | Ac5c | Arg | Phe-$NH_2$ | 18.5 | 632 | SEQ ID NO. 26 |
| PICM29 | Ac | Arg | Ac5c | Arg | Tyr-$NH_2$ | 18.2 | 648 | SEQ ID NO. 27 |
| PICM30 | Ac | Arg | Ac5c | Arg | Trp-$NH_2$ | 19.4 | 671 | SEQ ID NO. 28 |
| PICM31 | Ac | Arg | Ac5c | N(Me)Arg | Phe-$NH_2$ | 19.3 | 646 | SEQ ID NO. 29 |
| PICM32 | Ac | Arg | Ac5c | N(Me)Arg | Tyr-$NH_2$ | 19.1 | 662 | SEQ ID NO. 30 |
| PICM33 | Ac | Arg | Ac5c | N(Me)Arg | Trp-$NH_2$ | 20.7 | 685 | SEQ ID NO. 31 |
| PICM34 | pGlu | Arg | Ac5c | N(Me)Arg | Phe-$NH_2$ | 17.6 | 714 | SEQ ID NO. 32 |
| PICM35 | pGlu | Arg | Ac5c | N(Me)Arg | Tyr-$NH_2$ | 17.4 | 730 | SEQ ID NO. 33 |
| PICM36 | pGlu | Arg | Ac5c | N(Me)Arg | Trp-$NH_2$ | 18.4 | 753 | SEQ ID NO. 34 |
| PICM37 | pGlu | Arg | Ac5c | Arg | Phe-$NH_2$ | 16.2 | 700 | SEQ ID NO. 35 |
| PICM38 | pGlu | Arg | Ac5c | Arg | Tyr-$NH_2$ | 16.0 | 716 | SEQ ID NO. 36 |
| PICM39 | pGlu | Arg | Ac5c | Arg | Trp-$NH_2$ | 17.1 | 739 | SEQ ID NO. 37 |
| PICM40 | Ac | Arg | Glu | Arg | Phe-OH | 11.7 | 651 | SEQ ID NO. 38 |
| PICM41 | Ac | Arg | Glu | Arg | Tyr-OH | 11.5 | 667 | SEQ ID NO. 39 |
| PICM42 | Ac | Arg | Glu | Arg | Trp-OH | 12.6 | 690 | SEQ ID NO. 40 |
| PICM43 | Ac | Arg | Glu | Arg(Me) | Tyr-OH | 12.3 | 681 | SEQ ID NO. 41 |
| PICM44 | pGlu | Arg | Glu | Arg(Me) | Phe-OH | 12.9 | 733 | SEQ ID NO. 42 |
| PICM45 | pGlu | Arg | Glu | Arg | Trp-OH | 14.5 | 572 | SEQ ID NO. 43 |
| PICM46 | Ac | Arg | Aib | Arg | Phe-OH | 15.7 | 607 | SEQ ID NO. 44 |
| PICM47 | Ac | Arg | Aib | Arg(Me) | Phe-OH | 16.6 | 621 | SEQ ID NO. 45 |
| PICM48 | pGlu | Arg | Aib | Arg(Me) | Tyr-OH | 14.6 | 705 | SEQ ID NO. 46 |
| PICM49 | pGlu | Arg | Aib | Arg | Trp-OH | 13.5 | 714 | SEQ ID NO. 47 |
| PICM50 | Ac | Arg | Ac5c | Arg | Phe-OH | 19.1 | 633 | SEQ ID NO. 48 |

TABLE 1-continued

Examples of the peptide sequences according to the invention and their characterisation

| Name | L1 | X1 | X2 | X3 | X4 | Rt (min) | MH+ | SEQ ID NO. |
|---|---|---|---|---|---|---|---|---|
| PICM51 | Ac | Arg | Ac5c | Arg(Me) | Tyr-OH | 18.9 | 663 | SEQ ID NO. 49 |
| PICM52 | pGlu | Arg | Ac5c | Arg(Me) | Trp-OH | 21.1 | 754 | SEQ ID NO. 50 |
| PICM53 | pGlu | Arg | Ac5c | Arg | Trp-OH | 20.3 | 740 | SEQ ID NO. 51 |
| PICM54 | Ac | N(Me)Arg | Aib | Arg | Phe-NH$_2$ | 16.5 | 618 | SEQ ID NO. 52 |
| PICM55 | Ac | N(Me)Arg | Aib | N(Me)Arg | Phe-NH$_2$ | 21.2 | 632 | SEQ ID NO. 53 |
| PICM56 | Ac | Arg | Aib | N(Me)Arg | Phe-NH$_2$ | 16.6 | 618 | SEQ ID NO. 54 |
| PICM57 | Ac | Arg | Aib | Arg | α(Me)Phe-NH$_2$ | 14.3 | 618 | SEQ ID NO. 55 |
| PICM58 | Ac | N(Me)Arg | Aib | Arg | α(Me)Phe-NH$_2$ | 15.2 | 632 | SEQ ID NO. 56 |
| PICM59 | Ac | N(Me)Arg | Aib | N(Me)Arg | α(Me)Phe-NH$_2$ | 18.3 | 646 | SEQ ID NO. 57 |
| PICM60 | Ac | Arg | Aib | N(Me)Arg | α(Me)Phe-NH$_2$ | 19.1 | 632 | SEQ ID NO. 58 |
| PICM61 | Ac-Aib | N(Me)Arg | Aib | Arg | Phe-NH$_2$ | 20.6 | 703 | SEQ ID NO. 59 |
| PICM62 | Ac-Aib | N(Me)Arg | Aib | N(Me)Arg | Phe-NH$_2$ | 21.5 | 717 | SEQ ID NO. 60 |
| PICM63 | Ac-Aib | Arg | Aib | N(Me)Arg | Phe-NH$_2$ | 20.5 | 703 | SEQ ID NO. 61 |
| PICM64 | Ac-Aib | Arg | Aib | Arg | α(Me)Phe-NH$_2$ | 15.3 | 703 | SEQ ID NO. 62 |
| PICM65 | Ac-Aib | N(Me)Arg | Aib | Arg | α(Me)Phe-NH$_2$ | 16.2 | 717 | SEQ ID NO. 63 |
| PICM66 | Ac-Aib | N(Me)Arg | Aib | N(Me)Arg | α(Me)Phe-NH$_2$ | 17.1 | 731 | SEQ ID NO. 64 |
| PICM67 | Ac-Aib | Arg | Aib | N(Me)Arg | α(Me)Phe-NH$_2$ | 17.8 | 717 | SEQ ID NO. 65 |

EXAMPLE 4

Dose-dependent inhibition of cell migration exerted by PICM57.

The effect of PICM57 described in example 3 on the cell migration of human fibrosarcoma HT1080 cells was tested. A Boyden chamber equipped with polycarbonate filters, having pores with a diameter of 8 μm (Nucleopore), free of polyvinylpyrrolidone and coated with 5 μg/ml of vitronectin (Promega), was used, as reported in the literature (Carriero et al., Cancer Res. 59, 5307, 1999). $3 \times 10^4$ cells, in serum-free DMEM (Dulbecco Modified Eagle Medium), were deposited in the upper compartment of the Boyden chamber. The lower chamber was packed with DMEM containing 10% FBS (Foetal Bovine Serum) as a source of chemotactics, in the presence of increasing concentrations of PICM57. The cells were incubated for 4 h at 37° C. in humidified air containing 5% $CO_2$. After incubation, the cells adhering to the upper surface of the filter were mechanically removed, and the migrated cells adhering to the lower surface of the filter were fixed in ethanol, stained with haematoxylin, and counted at 200× in 10 fields/filter chosen at random. The directional migration in response to FBS in the absence of PICM57 was taken as 100% and the effect of PICM57 on cell migration was evaluated in percentage terms. The data represent the average of three independent experiments conducted in duplicate. The antagonistic effect of PICM57 on migration of HT1080 cells towards FBS is dose-dependent (Table 2). It begins at concentrations of 1 aM, reaches 50% of its maximum value at concentrations of 1 fM, and reaches the maximum effect at concentrations of 10 fM (66% of inhibition).

The mobility induced by FBS in the presence of Metastin [45-54] was evaluated under the same experimental conditions (Table 3). The data demonstrate that Metastin[45-54] concentrations 1,000 times greater than PICM57 (10 nM Metastin[45-54] vs. 10 fM PICM57 are required to obtain comparable levels of inhibition of directional migration towards FBS.

TABLE 2

Inhibiting effect of PICM57 on the directional migration of human fibrosarcoma HT1080 cells induced by 10% FBS, calculated as a percentage of the migrated cells toward 10% FBS alone (considered 100%)

| | PICM57 concentration | | | | | | | | | | | | |
|---|---|---|---|---|---|---|---|---|---|---|---|---|---|
| | 0 | 1 aM | 10 aM | 100 aM | 1 fM | 10 fM | 100 fM | 1 pM | 10 pM | 100 pM | 1 nM | 10 nM | 100 nM |
| Cell Migration towards 10% FBS (%) | 100 | 69 | 54 | 63 | 43 | 39 | 35 | 37 | 41 | 33 | 37 | 32 | 34 |

TABLE 3

Comparison of the inhibiting effects of PICM57, PICM1 and Metastin [45-54] on the directional migration of HT1080 cells induced by 10% FBS, expressed as a percentage of the migrated cells compared with the control (10% FBS).

| Concentration | Metastin [45-54] | PICM1 | PICM57 |
|---|---|---|---|
| 0 | 100 | 100 | 100 |
| 1 aM | 100 | 99 | 70 |
| 10 aM | 83 | 70 | 54 |
| 10 fM | 73 | 56 | 39 |
| 10 pM | 53 | 46 | 36 |
| 10 nM | 56 | 35 | 32 |

EXAMPLE 5

Inhibition of cell motility induced by PICM1 independently of the species or histogenetic origin of the cell lines.

Cell lines of human or murine origin, derived from various tissues, were subjected to in vitro directional migration tests employing Boyden chambers as described in example 4, and using 10% FBS as chemotactic source, in the presence/absence of 100 pM PICM1. Directional migration in response to FBS in the absence of PICM1 was taken as 100%, and the effect of PICM1 on cell migration was evaluated as a percentage of said value. The data represent the average of two independent experiments conducted in duplicate. In all the cell lines tested, an inhibiting effect of PICM1 on cell migration was observed (Table 4). Although the extent of the inhibition differs between the cell lines used, it was never less than 50%, and was also observed in murine melanoma B16 cells, which are unresponsive to Metastin (Ohtaki, T., et al. (2001) *Nature* 411, 613-617).

TABLE 4

Inhibiting effect of PICM1 peptide on the motility of various tumour cell lines of human or murine origin induced by 10% FBS, expressed as a percentage of the migrated cells compared with the control (10% FBS).

| Origin | Name of cell line | Histogenesis | 10% FBS 100 pM PICM1 |
|---|---|---|---|
| Human | MCF-7 | Breast cancer | 37 |
| Human | MDA-MB-231 | Breast cancer | 47 |
| Human | A431 | Skin cancer | 49 |
| Human | HeLa | Cervical adenocarcinoma | 48 |
| Human | U937 | Monocytic leukaemia | 39 |
| Human | M14 | Melanoma | 59 |
| Human | HT1080 | Fibrosarcoma | 34 |
| Human | Saos2 | Osteosarcoma | 43 |
| Murine | B16 | Melanoma | 50 |

EXAMPLE 6

Inhibition of motility of cells pre-incubated with PICM57.

Human fibrosarcoma HT1080 cells were incubated with DMEM, or with DMEM containing 100 pM PICM57, for 0, 15, 30, 60, or 120 min. The cells were: a) washed with PBS (Phosphate Buffered Saline); b) washed for 5 minutes at 23° C. with 50 mM glycine-HCl buffer pH 3.0 to remove the peptides from the cell surface (Carriero. et al. *Clin. Cancer Res.* 8, 1299-1308, 1997), and then with PBS. The cells were re-suspended in DMEM and subjected to cell migration tests in Boyden chambers as described in example 4, using 10% FBS as chemoattractant. The results (Table 5) are expressed as a percentage of the cells that migrated in the absence of FBS (basal migration), taken as 100%. The data represent the average of two independent experiments conducted in duplicate. Simple pre-incubation of the cells at PICM57 drastically reduces their ability to migrate towards FBS. 15 minutes' exposure is enough for the inhibition to become comparable with that described in example 4. Acid treatment after exposure of the cells to 100 pM PICM57 for 15 or 30 min entirely abolishes the inhibiting effects of PICM57 on cell motility.

TABLE 5

Inhibiting effect of peptide PICM57 on the motility of human fibrosarcoma HT1080 cells pre-incubated with PICM57 and exposed to a gradient of 10% FBS.

| Pre-incubation (min) | Cell Migration (% of basal migration) | |
|---|---|---|
| | Without Acid Washing | With Acid Washing |
| 0 | 100 | 100 |
| 0 | 393 | 362 |
| 15 | 98 | 367 |
| 30 | 103 | 350 |
| 60 | 112 | ND |
| 120 | 120 | ND |

EXAMPLE 7

The effect of peptide PICM57 on cell migration was tested in a Boyden chamber as described in example 4, using rat basophilic leukemia cells RBL-2H3 lacking the receptor with high affinity for the formylated peptide of bacterial origin fMLP (N-formyl-Met-Leu-Phe) (Le, Y, Gong, W., Tiffany, H.L., Tumanov, A., Nedospasov, S., Shen, W., Dunlop, N. M. Gao, J.L., Murphy, P.M., Oppenheim, J.J. Wang, J.M. Amyloid (beta)42 activates a G-protein-coupled chemoattractant receptor, FPR-like 1. J. Neurosci. 21, RC123, 2001) 50 µg/ml fibronectin or 10 nM fMLP was used as chemoattractant. The results are expressed as the percentage of cells that migrated in the absence of FBS (basal migration), taken as 100%. The data represent the average of two independent experiments conducted in duplicate. In agreement with the findings reported in the literature, RBL-2H3 cells migrate towards fibronectin but not towards fMLP. The addition 100 pM PICM57 to the chemotactic gradient does not reduce fibronectin-dependent cell migration (Table 6). Conversely, RBL-2H3 cells stably transfected with the cDNA of FPR (RBL-2H3/ETFR) acquire the ability to migrate in a gradient constituted by 10 nM fMLP. The addition to the chemotactic gradient of 100 pM of PICM57 does not reduce the fibronectin-dependent cell migration, but reduces cell migration towards fMLP to basal levels (Table 6). The definitive demonstration that the target of PIC57 is FPR derives from the observation that in binding assays, the binding of the fluorescinated peptide formyl-Nle-Leu-Phe-Nle-Tyr-Lys SEQ ID NO. 68 (Molecular Probes) to the surface of the RBL-2H3/ETFR cells is specifically reduced by 60% by pre-incubating the cells with 10 µM PICM57. Pre-incubation of the cells with 10 µM Metastin[45-54] does not modify the bond of the fluorescinated derivative formyl-Nle-Leu-Phe-Nle-Tyr-Lys SEQ ID NO. 68 peptide to the surface of the RBL-2H3/ETFR cells.

TABLE 6

Inhibition exerted by PICM57 on fMLP-dependent cell motility of RBL-2H3/ETFR cells.

| Chemotactic | Cell migration (% of basal migration) | | | |
|---|---|---|---|---|
| | RBL-2H3 | RBL-2H3 PICM57 | RBL-2H3/ ETFR | RBL-2H3/ETFR PICM57 |
| — | 100 | 100 | 100 | 100 |
| 10 nM fMLP | 103 | 102 | 270 | 99 |
| 50 µg/ml fibronectin | 272 | 275 | 220 | 215 |

EXAMPLE 8

Effect of PICM57 on cell proliferation.

Human fibrosarcoma HT1080 cells ($1\times10^3$ cells/well) were plated in DMEM 10% FBS using 96-well plates in the presence/absence of 100 pM or 100 nM PICM57. At times 24, 48, 72 or 96 h the non-adhering cells were removed, and after repeated rinses with PBS, the cells adhering to the plate were fixed and then stained with a sterile solution containing 1 mg/ml of MTT (3-(4,5-dimethylthiazolyl-2)-2,5-diphenyltetrazolium bromide, Sigma) for 4 h at 37° C. The stain was then removed with 100 µl of dimethyl sulphoxide and the corresponding optical density was read spectrophotometrically at 540 nm. The presence of PICM57 at both concentrations did not modify the proliferation index (duplication time approx. 18 h) of the HT1080 cells at any of the times examined (Table 7). The same result was obtained in parallel experiments, when the medium was removed and fresh solutions of 10% FBS/PICM57 were added to the cells every day for 4 consecutive days.

TABLE 7

Effect of peptide PICM57 on FBS-dependent proliferation of human fibrosarcoma HT1080 cells, evaluated by spectrophotometric optical density reading (λ: 540 nm).

| Time (h) | FBS (OD) | FBS/ 100 pM PICM57 (OD) | FBS/100 pM PICM57 reached every 24 h (OD) | FBS/ 100 nM PICM57 (OD) | FBS/100 nM PICM57 reached every 24 hours (OD) |
|---|---|---|---|---|---|
| 48 | 0.5 | 0.45 | 0.51 | 0.53 | 0.56 |
| 72 | 0.94 | 0.92 | 1.07 | 1.05 | 1 |
| 96 | 2.1 | 2.02 | 2.3 | 2.18 | 2.2 |

EXAMPLE 9

Effect of PICM1 and PICM57 on the invasiveness of human fibrosarcoma HT1080 cells.

The in vitro cell invasion tests were conducted with Boyden chambers, using polyvinylpyrrolidone free filters, having pores with a diameter of 8 µm (Nucleopore), coated with 70 µg/filter of matrigel and DMEM containing 10% FBS as chemoattractant (Silvestri et al. *Int. J. Cancer* 102, 562-571, 2002). Human fibrosarcoma HT1080 cells ($2\times10^5$ cells/sample) were deposited in the upper compartment of the chamber in a serum-free culture medium. The lower compartment of the chamber contained DMEM with the addition of 10% FBS as chemotactic source, and the peptides to be assayed, tested at the concentration indicated. The chambers, thus assembled, were placed at 37° C. in a humidified environment containing 5% $CO_2$. After 18 hrs, the cells which had crossed the matrigel and adhered to the lower surface of the filters were fixed, stained and counted. The data represent the average of two independent experiments conducted in duplicate. The results, set out in Table 8, are expressed as the percentage of cells that invade the matrigel in the presence of FBS, but in the absence of peptide (100%). The inhibiting effect of PICM1 and PICM57 on the invasiveness of HT1080 cells is dose-dependent.

TABLE 8

Dose-response inhibiting effect of PICM1 and PICM57 on invasion by human fibrosarcoma HT1080 cells induced by 10% FBS.

Cell invasion towards 10% FBS (%)

| Peptide concentration | PICM1 | PICM57 |
|---|---|---|
| 0 | 100 | 100 |
| 1 aM | 100 | 69 |
| 10 aM | 101 | 59 |
| 10 fM | 62 | 41 |
| 10 pM | 55 | 37 |
| 10 nM | 44 | 31 |

EXAMPLE 10

Inhibiting Effect of PICM1 and PICM57 on Neo-Angiogenesis In Vitro

The in vitro neo-angiogenesis tests were conducted by exploiting the ability of endothelial cells to form, in the presence of pro-angiogenic factors, cords which extend to form a network of microtubules on a layer of polymerised matrigel. For this type of assay, $5\times10^4$ HUVEC cells (Human Umbilical Vein Endothelial Cells) per well were plated in 24-well plates, in which 300 µl of matrigel was left to polymerise in the presence of 40 ng/ml of VEGF (Vascular Endothelial Growth Factor), used as pro-angiogenic agent, and the peptides indicated, at different concentrations. Tubule formation was evaluated after 18 hours' incubation at 37° C. in 5% $CO_2$, by counting the number of tubular structures in at least 5 fields, chosen at random, with an inverted microscope. The effect of the peptides on VEGF-dependent tubule-forming activity is calculated as a percentage of the number of tubular structures counted in the presence of VEGF (taken as 100%). The data (Table 9) represent the average of two experiments conducted in duplicate. The antagonistic effect of PICM1 and PICM57 on neo-angiogenesis in vitro is dose-dependent. This effect begins at concentrations of aM and reaches the peak action at a concentration of pM (20% of the number of tubular structures counted); 50% of the maximum effect is reached at concentrations of fM. The anti-angiogenic effect exerted by 50 nM of endostatin and the low inhibitory effect exerted by metastin[45-54] are shown by way of comparison.

TABLE 9

Dose-dependent inhibiting effect of PICM1 and PICM57 on the VEGF-dependent tubule-forming activity of HUVEC endothelial cells.

VEGF-dependent tubule-forming activity (%)

| Peptide concentration | PICM57 | PICM1 | Endostatin | Metastin [45-54] |
|---|---|---|---|---|
| 0 | 100 | 100 | ND | 100 |
| 1 aM | 96 | 104 | ND | ND |
| 10 aM | 75 | 77 | ND | ND |
| 10 fM | 53 | 65 | ND | 90 |
| 10 pM | 23 | 30 | ND | 63 |
| 10 nM | 19 | 22 | 30 | 65 |

EXAMPLE 11

Toxicity of PICM57

Acute toxicity tests of PICM57 on the mouse demonstrate an LD50 of 30 mg/Kg, clustered in the interval between 28 mg/Kg (all animals alive) and 32 mg/Kg (all animals dead). Acute toxicity tests of PICM57 on the rat demonstrate an LD50 of 65 mg/Kg, clustered in the interval between 58 mg/Kg (all animals alive) and 70 mg/Kg (all animals dead).

EXAMPLE 12

Anti-Metastatic Effect In Vivo

The anti-metastatic power of PICM1 was evaluated on an animal model. $2 \times 10^6$ human fibrosarcoma HT1080 cells, which cause pulmonary metastasis in the experimental model (Schweinitz A, et al., *J. Biol. Chem.* 279:33613, 2004), were suspended in saline solution and injected into the caudal vein of twenty 7-week-old CD1 nude mice. 24 hours after the inoculation of the tumour cells, groups of 10 animals were treated with a slow injection of 3 mg/Kg of PICM1, dissolved in 100 µl of saline solution, every 48 h, with the animal immobilised. The 10 control animals received the same injection treatment, but with the saline solution only. Each animal was weighed and inspected for dyspnoea every day. The control animals showed clear signs of respiratory difficulty after 22 days. All the treated and control animals were sacrificed, and an autopsy was conducted. The lungs, liver, kidneys, spleen and heart were subjected to macroscopic and microscopic analysis. None of the organs examined, of the controlled or treated animals, presented any histo-morphological alterations, with the exception of the lungs. However, macroscopic analysis of the lungs indicated extensive subpleural neoformations in the control animals, often with necrotic and haemorrhagic characteristics, which were not observed in the treated animals. At microscopic level, serial sections of the pulmonary biopsies of the control animals showed that 45% of the parenchymal area on average was occupied by metastatic nodules, often perivascular, with a central necrotic area. Conversely, on microscopic observation the animals treated with 3 mg/Kg of PICM1 did not exhibit the presence of metastasis.

The invention claimed is:

1. Peptides, in salt form or non-salt form, with the general formula $L_1-X_1-X_2-X_3-X_4$, wherein:

$L_1$ is acyl, Glu, Gln, said Glu and Gln being optionally N-acylated or N-alkylated and/or Cα-alkylated, Pro, hydroxy-Pro, Azt, Pip, pGlu, said pGlu being optionally N-acylated and/or Cα-alkylated, Aib, Ac3c, Ac4c, Ac5c or Ac6c, said Aib, Ac3c, Ac4c, Ac5c or Ac6c being optionally N-acylated or N-alkylated;

$X_1$ and $X_3$, which are equal or different, optionally N-alkylated and/or Cα-alkylated, are selected from Arg, Orn, Lys, and phenylalanine substituted in the meta or para positions with an amine or guanidine group;

$X_2$ is chosen from among Glu, Lys, said Glu and Lys being optionally N-alkylated and/or Cα-alkylated, Aib, Ac3c, Ac4c, Ac5c and Ac6c, said Aib, Ac3c, Ac4c, Ac5c and Ac6c being optionally N-alkylated;

$X_4$ is chosen from among Phe, h-Phe, Tyr, Trp, 1-Nal, 2-Nal, h-1-Nal, h-2-Nal, Cha, Chg and Phg, said Phe, h-Phe, Tyr, Trp, 1-Nal, 2-Nal, h-1-Nal, h-2-Nal, Cha, Chg and Phg being optionally amidated and/or Cα-alkylated, with the proviso that when $X_1$ is Arg, $X_2$ is Glu, $X_3$ is Lys and $X_4$ is Tyr, $L_1$ cannot be Pro.

2. Peptides as claimed in claim 1, wherein the acyl, or N acylating, N-alkylating, or Cα-alkylating groups contain 1 to 9 carbon atoms, and amidating C-terminal groups contain 0 to 14 carbon atoms.

3. Peptides as claimed in claim 1, wherein the acyl or N-alkylating groups contain 1 or 2 carbon atoms, and amidating C-terminal groups contains 0 to 5 carbon atoms.

4. Pharmaceutical compositions comprising one of the peptides claimed in claim 1, in association with suitable vehicles or excipients.

5. A method for the prevention or treatment of disorders associated with altered cell migration comprising administering an effective amount of a peptide of claim 1 to a human in need thereof.

6. Method as claimed in claim 5, wherein said effective amount is from 0.1 μg to 1 g per dose.

7. Method as claimed in claim 5, wherein said effective amount is between 0.1 mg and 100 mg per dose.

8. Method as claimed in claim 5 for the prevention or treatment of local or metastatic invasion by malignant tumors.

9. Method as claimed in claim 5, for the prevention or treatment of disorders associated with neo-angiogenesis.

10. Method as claimed in claim 5, for the prevention or treatment of disorders supported by cell migration and associated with chronic inflammation.

11. Method as claimed in claim 5, for the prevention or treatment of diseases associated with herpes virus infection.

12. Method as claimed in claim 9, wherein said disorders comprise retinal vasculopathies, retinopathies, macular degeneration and edema, or Kaposi's sarcoma.

13. Method as claimed in claim 10, wherein said disorders comprise autoimmune diseases, rheumatoid arthritis, psoriasis or chronic granulomatous disorders.

14. Peptides as claimed in claim 1, optionally in salt form, with the sequence: Ac-Arg-Glu-Arg-Phe-NH$_2$ SEQ ID NO. 66; pGlu-Arg-Glu-Arg-Tyr-OH SEQ ID NO. 67; Glu-Arg-Glu-Arg-Phe-NH$_2$ SEQ ID NO. 1; Ac-Arg-Glu-Arg-Tyr-NH$_2$ SEQ ID NO. 2; Ac-Arg-Glu-Arg-Trp-NH$_2$ SEQ ID NO. 3; Ac-Arg-Glu-N(Me)Arg-Phe-NH$_2$ SEQ ID NO. 4;

Ac-Arg-Glu-N(Me)Arg-Tyr-NH$_2$ SEQ ID NO. 5; Ac-Arg-Glu-N(Me)Arg-Trp-NH$_2$ SEQ ID NO.6; pGlu-Arg-Glu-N(Me)Arg-Phe-NH$_2$SEQ ID NO. 7; pGlu-Arg-Glu-N(Me)Arg-Tyr-NH$_2$ SEQ ID NO. 8; pGlu-Arg-Glu-N(Me)Arg-Trp-NH$_2$ SEQ ID NO. 9; pGlu-Arg-Glu-Arg-Phe-NH$_2$ SEQ ID NO. 10; pGlu-Arg-Glu-Arg-Tyr-NH$_2$ SEQ ID NO. 11; pGlu-Arg-Glu-Arg-Trp-NH$_2$ SEQ ID NO. 12; Ac-Arg-Aib-Arg-Phe-NH$_2$ SEQ ID NO. 13; Ac-Arg-Aib-Arg-Tyr-NH$_2$ SEQ ID NO. 14;

Ac-Arg-Aib-Arg-Trp-NH$_2$ SEQ ID NO. 15; Ac-Aib -Arg-Aib-Arg-Phe-NH$_2$ SEQ ID NO. 16;

Ac-Arg-Aib-N(Me)Arg-Phe-NH$_2$ SEQ ID NO. 17; Ac-Arg-Aib-N(Me)Arg-Tyr-NH$_2$ SEQ ID NO. 18; Ac-Arg-Aib-N(Me)Arg-Trp-NH$_2$ SEQ ID NO. 19;pGlu-Arg-Aib-N(Me)Arg-Phe-NH$_2$ SEQ ID NO. 20; Glu-Arg-Aib-N(Me)Arg-Tyr-NH$_2$ SEQ ID NO. 21; pGlu-Arg-Aib-N(Me)Arg-Trp-NH$_2$ SEQ ID NO. 22; pGlu-Arg-Aib-Arg-Phe-NH$_2$ SEQ ID NO. 23; pGlu-Arg-Aib-Arg-Tyr-NH$_2$ SEQ ID NO. 24; pGlu-Arg-Aib-Arg-Trp-NH$_2$ SEQ ID NO. 25; Ac-Arg-Ac5c-Arg-Phe-NH$_2$ SEQ ID NO. 26; Ac-Arg-Ac5c-Arg-Tyr-NH$_2$ SEQ ID NO. 27; Ac-Arg-Ac5c-Arg-Trp-NH$_2$ SEQ ID NO. 28; Ac-Arg-Ac5c-N(Me)Arg-Phe-NH$_2$ SEQ ID NO. 29; Ac-Arg-Ac5c-N(Me)Arg- Tyr-NH$_2$ SEQ ID NO. 30; Ac-Arg-Ac5c-N(Me)Arg-Trp-NH$_2$ SEQ ID NO. 31; pGlu-Arg-Ac5c-N (Me)Arg-Phe-NH$_2$ SEQ ID NO. 32; pGlu-Arg-Ac5c-N(Me)Arg-Tyr-NH$_2$ SEQ ID NO. 33; pGlu-Arg-Ac5c-N(Me)Arg-Trp-NH$_2$ SEQ ID NO. 34; pGlu-Arg-Ac5c-Arg-Phe-NH$_2$ SEQ ID NO. 35; pGlu-Arg-Ac5c-Arg-Tyr-NH$_2$ SEQ ID NO. 36; pGlu-Arg-Ac5c-Arg-Trp-NH$_2$ SEQ ID NO. 37; Ac-Arg-Glu-Arg-Phe-OH SEQ ID NO. 38; Ac-Arg-Glu-Arg-Tyr-OH SEQ ID NO. 39;

Ac-Arg-Glu-Arg-Trp-OH SEQ ID NO. 40; Ac-Arg-Glu-N(Me)Arg-Tyr-OH SEQ ID NO. 41;

pGlu-Arg-Glu-N(Me)Arg-Phe-OH SEQ ID NO. 42; pGlu-Arg-Glu-Arg-Trp-OH SEQ ID NO. 43; Ac-Arg-Aib-Arg-Phe-OH SEQ ID NO. 44; Ac-Arg-Aib-N(Me)Arg-Phe-OH SEQ ID NO. 45; pGlu-Arg-Aib-N(Me)Arg-Tyr-OH SEQ ID NO. 46; pGlu-Arg-Aib-Arg-Trp-OH SEQ ID NO. 47; Ac-Arg-Ac5c-Arg-Phe-OH SEQ ID NO. 48; Ac-Arg-Ac5c-N(Me)Arg-Tyr-OH SEQ ID NO. 49; pGlu-Arg-Ac5c-N(Me)Arg-Trp-OH SEQ ID NO. 50; pGlu-Arg-Ac5c-Arg-Trp-OH SEQ ID NO. 51; Ac—N(Me)Arg-Aib-Arg-Phe-NH$_2$ SEQ ID NO. 52; Ac—N(Me)Arg-Aib-N (Me)Arg-Phe-NH$_2$ SEQ ID NO. 53; Ac-Arg-Aib-N(Me)Arg-Phe-NH$_2$ SEQ ID NO. 54; Ac-Arg-Aib-Arg-α(Me)Phe-NH$_2$ SEQ ID NO. 55; Ac—N(Me)Arg-Aib-Arg-α(Me)Phe-NH$_2$ SEQ ID NO. 56; Ac—N(Me)Arg-Aib-N(Me)Arg-α(Me)Phe-NH$_2$ SEQ ID NO. 57; Ac-Arg-Aib-N Me)Arg-α(Me)Phe-NH$_2$ SEQ ID NO. 58; Ac-Aib-N(Me)Arg-Aib-Arg-Phe-NH$_2$ SEQ ID NO. 59; Ac-Aib-N(Me)Arg-Aib-N(Me)Arg-Phe-NH$_2$ SEQ ID NO. 60; Ac-Aib-Arg-Aib-N(Me)Arg-Phe-NH$_2$ SEQ ID NO. 61; Ac-Aib-Arg-Aib-Arg-α(Me)Phe-NH$_2$ SEQ ID NO. 62; Ac-Aib-N (Me)Arg-Aib-Arg-α(Me)Phe-NH$_2$ SEQ ID NO. 63; Ac-Aib-N (Me)Arg-Aib-N(Me)Arg-α(Me)Phe-NH$_2$ SEQ ID NO. 64; or Ac-Aib-Arg-Aib-N(Me)Arg-α(Me)Phe-NH$_2$ SEQ ID NO. 65.

* * * * *

SEQUENCE LISTING

```
<160> NUMBER OF SEQ ID NOS: 68

<210> SEQ ID NO 1
<211> LENGTH: 5
<212> TYPE: PRT
<213> ORGANISM: Artificial
<220> FEATURE:
<223> OTHER INFORMATION: synthetic peptide
<220> FEATURE:
<221> NAME/KEY: MOD_RES
<222> LOCATION: (5)..(5)
<223> OTHER INFORMATION: AMIDATION

<400> SEQUENCE: 1

Glu Arg Glu Arg Phe
1               5

<210> SEQ ID NO 2
<211> LENGTH: 4
<212> TYPE: PRT
<213> ORGANISM: Artificial
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (4)..(4)
<223> OTHER INFORMATION: AMIDATION

<400> SEQUENCE: 2

Arg Glu Arg Tyr
1

<210> SEQ ID NO 3
<211> LENGTH: 4
<212> TYPE: PRT
<213> ORGANISM: Artificial
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (4)..(4)
<223> OTHER INFORMATION: AMIDATION
```

```
<400> SEQUENCE: 3

Arg Glu Arg Trp
1

<210> SEQ ID NO 4
<211> LENGTH: 4
<212> TYPE: PRT
<213> ORGANISM: Artificial
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (3)..(3)
<223> OTHER INFORMATION: X is N(Me) Arg
<220> FEATURE:
<221> NAME/KEY: MOD_RES
<222> LOCATION: (4)..(4)
<223> OTHER INFORMATION: AMIDATION

<400> SEQUENCE: 4

Arg Glu Xaa Phe
1

<210> SEQ ID NO 5
<211> LENGTH: 4
<212> TYPE: PRT
<213> ORGANISM: Artificial
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (3)..(3)
<223> OTHER INFORMATION: X is N(Me)Arg
<220> FEATURE:
<221> NAME/KEY: MOD_RES
<222> LOCATION: (4)..(4)
<223> OTHER INFORMATION: AMIDATION

<400> SEQUENCE: 5

Arg Glu Xaa Tyr
1

<210> SEQ ID NO 6
<211> LENGTH: 4
<212> TYPE: PRT
<213> ORGANISM: Artificial
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (3)..(3)
<223> OTHER INFORMATION: X is N(Me)Arg
<220> FEATURE:
<221> NAME/KEY: MOD_RES
<222> LOCATION: (4)..(4)
<223> OTHER INFORMATION: AMIDATION

<400> SEQUENCE: 6

Arg Glu Xaa Trp
1
```

```
<210> SEQ ID NO 7
<211> LENGTH: 5
<212> TYPE: PRT
<213> ORGANISM: Artificial
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: X is pGlu
<220> FEATURE:
<221> NAME/KEY: MOD_RES
<222> LOCATION: (4)..(4)
<223> OTHER INFORMATION: X is N(Me)Arg
<220> FEATURE:
<221> NAME/KEY: MOD_RES
<222> LOCATION: (5)..(5)
<223> OTHER INFORMATION: AMIDATION

<400> SEQUENCE: 7

Xaa Arg Glu Xaa Phe
1               5

<210> SEQ ID NO 8
<211> LENGTH: 5
<212> TYPE: PRT
<213> ORGANISM: Artificial
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: X is pGlu
<220> FEATURE:
<221> NAME/KEY: MOD_RES
<222> LOCATION: (4)..(4)
<223> OTHER INFORMATION: X is N(Me)Arg
<220> FEATURE:
<221> NAME/KEY: MOD_RES
<222> LOCATION: (5)..(5)
<223> OTHER INFORMATION: AMIDATION

<400> SEQUENCE: 8

Xaa Arg Glu Xaa Tyr
1               5

<210> SEQ ID NO 9
<211> LENGTH: 5
<212> TYPE: PRT
<213> ORGANISM: Artificial
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: X is pGlu
<220> FEATURE:
<221> NAME/KEY: MOD_RES
<222> LOCATION: (4)..(4)
<223> OTHER INFORMATION: X is N(Me)Arg
<220> FEATURE:
<221> NAME/KEY: MOD_RES
<222> LOCATION: (5)..(5)
<223> OTHER INFORMATION: AMIDATION

<400> SEQUENCE: 9

Xaa Arg Glu Xaa Trp
1               5

<210> SEQ ID NO 10
<211> LENGTH: 5
<212> TYPE: PRT
```

```
<213> ORGANISM: Artificial
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: X is pGlu
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: MOD_RES
<222> LOCATION: (5)..(5)
<223> OTHER INFORMATION: AMIDATION

<400> SEQUENCE: 10

Xaa Arg Glu Xaa Phe
1               5

<210> SEQ ID NO 11
<211> LENGTH: 5
<212> TYPE: PRT
<213> ORGANISM: Artificial
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: X is pGlu
<220> FEATURE:
<221> NAME/KEY: MOD_RES
<222> LOCATION: (5)..(5)
<223> OTHER INFORMATION: AMIDATION

<400> SEQUENCE: 11

Xaa Arg Glu Arg Tyr
1               5

<210> SEQ ID NO 12
<211> LENGTH: 5
<212> TYPE: PRT
<213> ORGANISM: Artificial
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: X is pGlu
<220> FEATURE:
<221> NAME/KEY: MOD_RES
<222> LOCATION: (5)..(5)
<223> OTHER INFORMATION: AMIDATION

<400> SEQUENCE: 12

Xaa Arg Glu Arg Trp
1               5

<210> SEQ ID NO 13
<211> LENGTH: 4
<212> TYPE: PRT
<213> ORGANISM: Artificial
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
```

```
<222> LOCATION: (4)..(4)
<223> OTHER INFORMATION: AMIDATION

<400> SEQUENCE: 13

Arg Xaa Arg Phe
1

<210> SEQ ID NO 14
<211> LENGTH: 4
<212> TYPE: PRT
<213> ORGANISM: Artificial
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (4)..(4)
<223> OTHER INFORMATION: AMIDATION

<400> SEQUENCE: 14

Arg Xaa Arg Tyr
1

<210> SEQ ID NO 15
<211> LENGTH: 4
<212> TYPE: PRT
<213> ORGANISM: Artificial
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (4)..(4)
<223> OTHER INFORMATION: AMIDATION

<400> SEQUENCE: 15

Arg Xaa Arg Trp
1

<210> SEQ ID NO 16
<211> LENGTH: 5
<212> TYPE: PRT
<213> ORGANISM: Artificial
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (1)..(1)
<223> OTHER INFORMATION: Aib
<220> FEATURE:
<221> NAME/KEY: MOD_RES
<222> LOCATION: (3)..(3)
<223> OTHER INFORMATION: Aib
<220> FEATURE:
<221> NAME/KEY: MOD_RES
<222> LOCATION: (5)..(5)
```

<223> OTHER INFORMATION: AMIDATION

<400> SEQUENCE: 16

Xaa Arg Xaa Arg Phe
1               5

<210> SEQ ID NO 17
<211> LENGTH: 4
<212> TYPE: PRT
<213> ORGANISM: Artificial
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (3)..(3)
<223> OTHER INFORMATION: X is N(Me)Arg
<220> FEATURE:
<221> NAME/KEY: MOD_RES
<222> LOCATION: (4)..(4)
<223> OTHER INFORMATION: AMIDATION

<400> SEQUENCE: 17

Arg Xaa Arg Phe
1

<210> SEQ ID NO 18
<211> LENGTH: 4
<212> TYPE: PRT
<213> ORGANISM: Artificial
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (3)..(3)
<223> OTHER INFORMATION: X is N(Me)Arg
<220> FEATURE:
<221> NAME/KEY: MOD_RES
<222> LOCATION: (4)..(4)
<223> OTHER INFORMATION: AMIDATION

<400> SEQUENCE: 18

Arg Xaa Xaa Tyr
1

<210> SEQ ID NO 19
<211> LENGTH: 4
<212> TYPE: PRT
<213> ORGANISM: Artificial
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (2)..(2)
<223> OTHER INFORMATION: Aib

```
<220> FEATURE:
<221> NAME/KEY: MOD_RES
<222> LOCATION: (3)..(3)
<223> OTHER INFORMATION: X is N(Me)Arg
<220> FEATURE:
<221> NAME/KEY: MOD_RES
<222> LOCATION: (4)..(4)
<223> OTHER INFORMATION: AMIDATION

<400> SEQUENCE: 19

Arg Xaa Xaa Trp
1

<210> SEQ ID NO 20
<211> LENGTH: 5
<212> TYPE: PRT
<213> ORGANISM: Artificial
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: X is pGlu
<220> FEATURE:
<221> NAME/KEY: MOD_RES
<222> LOCATION: (3)..(3)
<223> OTHER INFORMATION: Aib
<220> FEATURE:
<221> NAME/KEY: MOD_RES
<222> LOCATION: (4)..(4)
<223> OTHER INFORMATION: X is N(Me)Arg
<220> FEATURE:
<221> NAME/KEY: MOD_RES
<222> LOCATION: (5)..(5)
<223> OTHER INFORMATION: AMIDATION

<400> SEQUENCE: 20

Xaa Arg Xaa Xaa Phe
1               5

<210> SEQ ID NO 21
<211> LENGTH: 5
<212> TYPE: PRT
<213> ORGANISM: Artificial
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: X is pGlu
<220> FEATURE:
<221> NAME/KEY: MOD_RES
<222> LOCATION: (3)..(3)
<223> OTHER INFORMATION: Aib
<220> FEATURE:
<221> NAME/KEY: MOD_RES
<222> LOCATION: (4)..(4)
<223> OTHER INFORMATION: X is N(Me)Arg
<220> FEATURE:
<221> NAME/KEY: MOD_RES
<222> LOCATION: (5)..(5)
<223> OTHER INFORMATION: AMIDATION

<400> SEQUENCE: 21

Xaa Arg Xaa Xaa Tyr
1               5

<210> SEQ ID NO 22
<211> LENGTH: 5
<212> TYPE: PRT
<213> ORGANISM: Artificial
<220> FEATURE:
<223> OTHER INFORMATION: synthetic peptide
<220> FEATURE:
```

```
<221> NAME/KEY: MOD_RES
<222> LOCATION: (1)..(1)
<223> OTHER INFORMATION: X is pGlu
<220> FEATURE:
<221> NAME/KEY: MOD_RES
<222> LOCATION: (3)..(3)
<223> OTHER INFORMATION: Aib
<220> FEATURE:
<221> NAME/KEY: MOD_RES
<222> LOCATION: (4)..(4)
<223> OTHER INFORMATION: X is N(Me)Aeg
<220> FEATURE:
<221> NAME/KEY: MOD_RES
<222> LOCATION: (5)..(5)
<223> OTHER INFORMATION: AMIDATION

<400> SEQUENCE: 22

Xaa Arg Xaa Xaa Trp
1               5

<210> SEQ ID NO 23
<211> LENGTH: 5
<212> TYPE: PRT
<213> ORGANISM: Artificial
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: pGlu
<220> FEATURE:
<221> NAME/KEY: MOD_RES
<222> LOCATION: (3)..(3)
<223> OTHER INFORMATION: Aib
<220> FEATURE:
<221> NAME/KEY: MOD_RES
<222> LOCATION: (5)..(5)
<223> OTHER INFORMATION: AMIDATION

<400> SEQUENCE: 23

Xaa Arg Xaa Arg Phe
1               5

<210> SEQ ID NO 24
<211> LENGTH: 5
<212> TYPE: PRT
<213> ORGANISM: Artificial
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: pGlu
<220> FEATURE:
<221> NAME/KEY: MOD_RES
<222> LOCATION: (3)..(3)
<223> OTHER INFORMATION: Aib
<220> FEATURE:
<221> NAME/KEY: MOD_RES
<222> LOCATION: (5)..(5)
<223> OTHER INFORMATION: AMIDATION

<400> SEQUENCE: 24

Xaa Arg Xaa Arg Tyr
1               5

<210> SEQ ID NO 25
<211> LENGTH: 5
<212> TYPE: PRT
<213> ORGANISM: Artificial
<220> FEATURE:
<223> OTHER INFORMATION: synthetic peptide
<220> FEATURE:
<221> NAME/KEY: MOD_RES
```

```
<222> LOCATION: (1)..(1)
<223> OTHER INFORMATION: pGlu
<220> FEATURE:
<221> NAME/KEY: MOD_RES
<222> LOCATION: (3)..(3)
<223> OTHER INFORMATION: Aib
<220> FEATURE:
<221> NAME/KEY: MOD_RES
<222> LOCATION: (5)..(5)
<223> OTHER INFORMATION: AMIDATION

<400> SEQUENCE: 25

Xaa Arg Xaa Arg Trp
1               5

<210> SEQ ID NO 26
<211> LENGTH: 4
<212> TYPE: PRT
<213> ORGANISM: Artificial
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (2)..(2)
<223> OTHER INFORMATION: 1-aminocyclopentan-1-carboxylic acid
<220> FEATURE:
<221> NAME/KEY: MOD_RES
<222> LOCATION: (4)..(4)
<223> OTHER INFORMATION: AMIDATION

<400> SEQUENCE: 26

Arg Xaa Arg Phe
1

<210> SEQ ID NO 27
<211> LENGTH: 4
<212> TYPE: PRT
<213> ORGANISM: Artificial
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (2)..(2)
<223> OTHER INFORMATION: 1-aminocyclopentan-1-carboxylic acid
<220> FEATURE:
<221> NAME/KEY: MOD_RES
<222> LOCATION: (4)..(4)
<223> OTHER INFORMATION: AMIDATION

<400> SEQUENCE: 27

Arg Xaa Arg Tyr
1

<210> SEQ ID NO 28
<211> LENGTH: 4
<212> TYPE: PRT
<213> ORGANISM: Artificial
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (2)..(2)
```

```
<223> OTHER INFORMATION: 1-aminocyclopentan-1-carboxylic acid
<220> FEATURE:
<221> NAME/KEY: MOD_RES
<222> LOCATION: (4)..(4)
<223> OTHER INFORMATION: AMIDATION

<400> SEQUENCE: 28

Arg Xaa Arg Trp
1

<210> SEQ ID NO 29
<211> LENGTH: 4
<212> TYPE: PRT
<213> ORGANISM: Artificial
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (2)..(2)
<223> OTHER INFORMATION: 1-aminocyclopentan-1-carboxylic acid
<220> FEATURE:
<221> NAME/KEY: MOD_RES
<222> LOCATION: (3)..(3)
<223> OTHER INFORMATION: N(Me)Arg
<220> FEATURE:
<221> NAME/KEY: MOD_RES
<222> LOCATION: (4)..(4)
<223> OTHER INFORMATION: AMIDATION

<400> SEQUENCE: 29

Arg Xaa Xaa Phe
1

<210> SEQ ID NO 30
<211> LENGTH: 4
<212> TYPE: PRT
<213> ORGANISM: Artificial
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (2)..(2)
<223> OTHER INFORMATION: 1-aminocyclopentan-1-carboxylic acid
<220> FEATURE:
<221> NAME/KEY: MOD_RES
<222> LOCATION: (3)..(3)
<223> OTHER INFORMATION: N(Me)Arg
<220> FEATURE:
<221> NAME/KEY: MOD_RES
<222> LOCATION: (4)..(4)
<223> OTHER INFORMATION: AMIDATION

<400> SEQUENCE: 30

Arg Xaa Xaa Tyr
1

<210> SEQ ID NO 31
<211> LENGTH: 4
<212> TYPE: PRT
<213> ORGANISM: Artificial
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: ACETYLATION
```

```
<220> FEATURE:
<221> NAME/KEY: MOD_RES
<222> LOCATION: (2)..(2)
<223> OTHER INFORMATION: 1-aminocyclopentan-1-carboxylic acid
<220> FEATURE:
<221> NAME/KEY: MOD_RES
<222> LOCATION: (3)..(3)
<223> OTHER INFORMATION: N(Me)Arg
<220> FEATURE:
<221> NAME/KEY: MOD_RES
<222> LOCATION: (4)..(4)
<223> OTHER INFORMATION: AMIDATION

<400> SEQUENCE: 31

Arg Xaa Xaa Trp
1

<210> SEQ ID NO 32
<211> LENGTH: 5
<212> TYPE: PRT
<213> ORGANISM: Artificial
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: pGlu
<220> FEATURE:
<221> NAME/KEY: MOD_RES
<222> LOCATION: (3)..(3)
<223> OTHER INFORMATION: 1-aminocyclopentan-1-carboxylic acid
<220> FEATURE:
<221> NAME/KEY: MOD_RES
<222> LOCATION: (4)..(4)
<223> OTHER INFORMATION: N(Me)Arg
<220> FEATURE:
<221> NAME/KEY: MOD_RES
<222> LOCATION: (5)..(5)
<223> OTHER INFORMATION: AMIDATION

<400> SEQUENCE: 32

Xaa Arg Xaa Xaa Phe
1               5

<210> SEQ ID NO 33
<211> LENGTH: 5
<212> TYPE: PRT
<213> ORGANISM: Artificial
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: X is pGLU
<220> FEATURE:
<221> NAME/KEY: MOD_RES
<222> LOCATION: (3)..(3)
<223> OTHER INFORMATION: 1-aminocyclopentan-1-carboxylic acid
<220> FEATURE:
<221> NAME/KEY: MOD_RES
<222> LOCATION: (4)..(4)
<223> OTHER INFORMATION: N(Me)Arg
<220> FEATURE:
<221> NAME/KEY: MOD_RES
<222> LOCATION: (5)..(5)
<223> OTHER INFORMATION: AMIDATION

<400> SEQUENCE: 33

Xaa Arg Xaa Xaa Tyr
1               5

<210> SEQ ID NO 34
<211> LENGTH: 5
<212> TYPE: PRT
```

```
<213> ORGANISM: Artificial
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: pGlu
<220> FEATURE:
<221> NAME/KEY: MOD_RES
<222> LOCATION: (3)..(3)
<223> OTHER INFORMATION: 1-aminocyclopentan-1-carboxylic acid
<220> FEATURE:
<221> NAME/KEY: MOD_RES
<222> LOCATION: (4)..(4)
<223> OTHER INFORMATION: N(Me)Arg
<220> FEATURE:
<221> NAME/KEY: MOD_RES
<222> LOCATION: (5)..(5)
<223> OTHER INFORMATION: AMIDATION

<400> SEQUENCE: 34

Xaa Arg Xaa Xaa Trp
1               5

<210> SEQ ID NO 35
<211> LENGTH: 5
<212> TYPE: PRT
<213> ORGANISM: Artificial
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: X is pGlu
<220> FEATURE:
<221> NAME/KEY: MOD_RES
<222> LOCATION: (3)..(3)
<223> OTHER INFORMATION: 1-aminocyclopentan-1-carboxylic acid
<220> FEATURE:
<221> NAME/KEY: MOD_RES
<222> LOCATION: (5)..(5)
<223> OTHER INFORMATION: AMIDATION

<400> SEQUENCE: 35

Xaa Arg Xaa Arg Phe
1               5

<210> SEQ ID NO 36
<211> LENGTH: 5
<212> TYPE: PRT
<213> ORGANISM: Artificial
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: X is pGlu
<220> FEATURE:
<221> NAME/KEY: MOD_RES
<222> LOCATION: (3)..(3)
<223> OTHER INFORMATION: 1-aminocyclopentan-1-carboxylic acid
<220> FEATURE:
<221> NAME/KEY: MOD_RES
<222> LOCATION: (5)..(5)
<223> OTHER INFORMATION: AMIDATION

<400> SEQUENCE: 36

Xaa Arg Xaa Arg Tyr
1               5

<210> SEQ ID NO 37
<211> LENGTH: 5
<212> TYPE: PRT
<213> ORGANISM: Artificial
```

```
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: X is pGlu
<220> FEATURE:
<221> NAME/KEY: MOD_RES
<222> LOCATION: (3)..(3)
<223> OTHER INFORMATION: 1-aminocyclopentan-1-carboxylic acid
<220> FEATURE:
<221> NAME/KEY: MOD_RES
<222> LOCATION: (5)..(5)
<223> OTHER INFORMATION: AMIDATION

<400> SEQUENCE: 37

Xaa Arg Xaa Arg Trp
1               5

<210> SEQ ID NO 38
<211> LENGTH: 4
<212> TYPE: PRT
<213> ORGANISM: Artificial
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: ACETYLATION

<400> SEQUENCE: 38

Arg Glu Arg Phe
1

<210> SEQ ID NO 39
<211> LENGTH: 4
<212> TYPE: PRT
<213> ORGANISM: Artificial
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: ACETYLATION

<400> SEQUENCE: 39

Arg Glu Arg Tyr
1

<210> SEQ ID NO 40
<211> LENGTH: 4
<212> TYPE: PRT
<213> ORGANISM: Artificial
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: ACETYLATION

<400> SEQUENCE: 40

Arg Glu Arg Trp
1

<210> SEQ ID NO 41
<211> LENGTH: 4
<212> TYPE: PRT
<213> ORGANISM: Artificial
<220> FEATURE:
<223> OTHER INFORMATION: synthetic peptide
<220> FEATURE:
<221> NAME/KEY: MOD_RES
```

-continued

```
<222> LOCATION: (1)..(1)
<223> OTHER INFORMATION: ACETYLATION
<220> FEATURE:
<221> NAME/KEY: MOD_RES
<222> LOCATION: (3)..(3)
<223> OTHER INFORMATION: Arg(Me)

<400> SEQUENCE: 41

Arg Glu Xaa Tyr
1

<210> SEQ ID NO 42
<211> LENGTH: 5
<212> TYPE: PRT
<213> ORGANISM: Artificial
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: X is pGlu
<220> FEATURE:
<221> NAME/KEY: MOD_RES
<222> LOCATION: (4)..(4)
<223> OTHER INFORMATION: Arg(Me)

<400> SEQUENCE: 42

Xaa Arg Glu Xaa Phe
1               5

<210> SEQ ID NO 43
<211> LENGTH: 5
<212> TYPE: PRT
<213> ORGANISM: Artificial
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: pGlu

<400> SEQUENCE: 43

Xaa Arg Glu Arg Trp
1               5

<210> SEQ ID NO 44
<211> LENGTH: 4
<212> TYPE: PRT
<213> ORGANISM: Artificial
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (2)..(2)
<223> OTHER INFORMATION: Aib

<400> SEQUENCE: 44

Arg Xaa Arg Phe
1

<210> SEQ ID NO 45
<211> LENGTH: 4
<212> TYPE: PRT
<213> ORGANISM: Artificial
<220> FEATURE:
<223> OTHER INFORMATION: synthetic peptide
<220> FEATURE:
<221> NAME/KEY: MOD_RES
```

```
<222> LOCATION: (1)..(1)
<223> OTHER INFORMATION: ACETYLATION
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (3)..(3)
<223> OTHER INFORMATION: Arg(Me)

<400> SEQUENCE: 45

Arg Xaa Xaa Phe
 1

<210> SEQ ID NO 46
<211> LENGTH: 5
<212> TYPE: PRT
<213> ORGANISM: Artificial
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: pGlu
<220> FEATURE:
<221> NAME/KEY: MOD_RES
<222> LOCATION: (3)..(3)
<223> OTHER INFORMATION: Aib
<220> FEATURE:
<221> NAME/KEY: MOD_RES
<222> LOCATION: (4)..(4)
<223> OTHER INFORMATION: Arg(Me)

<400> SEQUENCE: 46

Xaa Arg Xaa Xaa Tyr
 1               5

<210> SEQ ID NO 47
<211> LENGTH: 5
<212> TYPE: PRT
<213> ORGANISM: Artificial
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: pGlu
<220> FEATURE:
<221> NAME/KEY: MOD_RES
<222> LOCATION: (3)..(3)
<223> OTHER INFORMATION: Aib

<400> SEQUENCE: 47

Xaa Arg Xaa Arg Trp
 1               5

<210> SEQ ID NO 48
<211> LENGTH: 4
<212> TYPE: PRT
<213> ORGANISM: Artificial
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (2)..(2)
<223> OTHER INFORMATION: 1-aminocyclopentan-1-carboxylic acid

<400> SEQUENCE: 48
```

Arg Xaa Arg Phe
1

<210> SEQ ID NO 49
<211> LENGTH: 4
<212> TYPE: PRT
<213> ORGANISM: Artificial
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (2)..(2)
<223> OTHER INFORMATION: 1-aminocyclopentan-1-carboxylic acid
<220> FEATURE:
<221> NAME/KEY: MOD_RES
<222> LOCATION: (3)..(3)
<223> OTHER INFORMATION: Arg(Me)

<400> SEQUENCE: 49

Arg Xaa Xaa Tyr
1

<210> SEQ ID NO 50
<211> LENGTH: 5
<212> TYPE: PRT
<213> ORGANISM: Artificial
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: pGlu
<220> FEATURE:
<221> NAME/KEY: MOD_RES
<222> LOCATION: (3)..(3)
<223> OTHER INFORMATION: 1-aminocyclopentan-1-carboxylic acid
<220> FEATURE:
<221> NAME/KEY: MOD_RES
<222> LOCATION: (4)..(4)
<223> OTHER INFORMATION: Arg(Me)

<400> SEQUENCE: 50

Xaa Arg Xaa Xaa Trp
1               5

<210> SEQ ID NO 51
<211> LENGTH: 5
<212> TYPE: PRT
<213> ORGANISM: Artificial
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: pGlu
<220> FEATURE:
<221> NAME/KEY: MOD_RES
<222> LOCATION: (3)..(3)
<223> OTHER INFORMATION: 1-aminocyclopentan-1-carboxylic acid

<400> SEQUENCE: 51

Xaa Arg Xaa Arg Trp
1               5

<210> SEQ ID NO 52
<211> LENGTH: 4
<212> TYPE: PRT
<213> ORGANISM: Artificial
<220> FEATURE:

-continued

<223> OTHER INFORMATION: synthetic peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (1)..(1)
<223> OTHER INFORMATION: N(Me)Arg
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (4)..(4)
<223> OTHER INFORMATION: AMIDATION

<400> SEQUENCE: 52

Xaa Xaa Arg Phe
1

<210> SEQ ID NO 53
<211> LENGTH: 4
<212> TYPE: PRT
<213> ORGANISM: Artificial
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (1)..(1)
<223> OTHER INFORMATION: N(Me)Arg
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (3)..(3)
<223> OTHER INFORMATION: N(Me)Arg
<220> FEATURE:
<221> NAME/KEY: MOD_RES
<222> LOCATION: (4)..(4)
<223> OTHER INFORMATION: AMIDATION

<400> SEQUENCE: 53

Xaa Xaa Xaa Phe
1

<210> SEQ ID NO 54
<211> LENGTH: 4
<212> TYPE: PRT
<213> ORGANISM: Artificial
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (3)..(3)
<223> OTHER INFORMATION: N(Me)Arg
<220> FEATURE:
<221> NAME/KEY: MOD_RES
<222> LOCATION: (4)..(4)
<223> OTHER INFORMATION: AMIDATION

```
<400> SEQUENCE: 54

Arg Xaa Xaa Phe
1

<210> SEQ ID NO 55
<211> LENGTH: 4
<212> TYPE: PRT
<213> ORGANISM: Artificial
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (4)..(4)
<223> OTHER INFORMATION: alpha(Me)Phe
<220> FEATURE:
<221> NAME/KEY: MOD_RES
<222> LOCATION: (4)..(4)
<223> OTHER INFORMATION: AMIDATION

<400> SEQUENCE: 55

Arg Xaa Arg Xaa
1

<210> SEQ ID NO 56
<211> LENGTH: 4
<212> TYPE: PRT
<213> ORGANISM: Artificial
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (1)..(1)
<223> OTHER INFORMATION: N(Me)Arg
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (4)..(4)
<223> OTHER INFORMATION: alpha(Me)Phe
<220> FEATURE:
<221> NAME/KEY: MOD_RES
<222> LOCATION: (4)..(4)
<223> OTHER INFORMATION: AMIDATION

<400> SEQUENCE: 56

Xaa Xaa Arg Xaa
1

<210> SEQ ID NO 57
<211> LENGTH: 4
<212> TYPE: PRT
<213> ORGANISM: Artificial
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
```

```
<222> LOCATION: (1)..(1)
<223> OTHER INFORMATION: N(Me)Arg
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (3)..(3)
<223> OTHER INFORMATION: N(Me)Arg
<220> FEATURE:
<221> NAME/KEY: MOD_RES
<222> LOCATION: (4)..(4)
<223> OTHER INFORMATION: alpha(Me)Phe
<220> FEATURE:
<221> NAME/KEY: MOD_RES
<222> LOCATION: (4)..(4)
<223> OTHER INFORMATION: AMIDATION

<400> SEQUENCE: 57

Xaa Xaa Xaa Xaa
1

<210> SEQ ID NO 58
<211> LENGTH: 4
<212> TYPE: PRT
<213> ORGANISM: Artificial
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (3)..(3)
<223> OTHER INFORMATION: N(Me)Arg
<220> FEATURE:
<221> NAME/KEY: MOD_RES
<222> LOCATION: (4)..(4)
<223> OTHER INFORMATION: alpha(Me)Phe
<220> FEATURE:
<221> NAME/KEY: MOD_RES
<222> LOCATION: (4)..(4)
<223> OTHER INFORMATION: AMIDATION

<400> SEQUENCE: 58

Arg Xaa Xaa Xaa
1

<210> SEQ ID NO 59
<211> LENGTH: 5
<212> TYPE: PRT
<213> ORGANISM: Artificial
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (1)..(1)
<223> OTHER INFORMATION: Aib
<220> FEATURE:
<221> NAME/KEY: MOD_RES
<222> LOCATION: (2)..(2)
<223> OTHER INFORMATION: N(Me)Arg
<220> FEATURE:
<221> NAME/KEY: MOD_RES
<222> LOCATION: (3)..(3)
<223> OTHER INFORMATION: Aib
```

```
<220> FEATURE:
<221> NAME/KEY: MOD_RES
<222> LOCATION: (5)..(5)
<223> OTHER INFORMATION: AMIDATION

<400> SEQUENCE: 59

Xaa Xaa Xaa Arg Phe
1               5

<210> SEQ ID NO 60
<211> LENGTH: 5
<212> TYPE: PRT
<213> ORGANISM: Artificial
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (1)..(1)
<223> OTHER INFORMATION: Aib
<220> FEATURE:
<221> NAME/KEY: MOD_RES
<222> LOCATION: (2)..(2)
<223> OTHER INFORMATION: N(Me)Arg
<220> FEATURE:
<221> NAME/KEY: MOD_RES
<222> LOCATION: (3)..(3)
<223> OTHER INFORMATION: Aib
<220> FEATURE:
<221> NAME/KEY: MOD_RES
<222> LOCATION: (4)..(4)
<223> OTHER INFORMATION: N(Me)Arg
<220> FEATURE:
<221> NAME/KEY: MOD_RES
<222> LOCATION: (5)..(5)
<223> OTHER INFORMATION: AMIDATION

<400> SEQUENCE: 60

Xaa Xaa Xaa Xaa Phe
1               5

<210> SEQ ID NO 61
<211> LENGTH: 5
<212> TYPE: PRT
<213> ORGANISM: Artificial
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (1)..(1)
<223> OTHER INFORMATION: Aib
<220> FEATURE:
<221> NAME/KEY: MOD_RES
<222> LOCATION: (3)..(3)
<223> OTHER INFORMATION: Aib
<220> FEATURE:
<221> NAME/KEY: MOD_RES
<222> LOCATION: (4)..(4)
<223> OTHER INFORMATION: N(Me)Arg
<220> FEATURE:
<221> NAME/KEY: MOD_RES
<222> LOCATION: (5)..(5)
<223> OTHER INFORMATION: AMIDATION

<400> SEQUENCE: 61

Xaa Arg Xaa Xaa Phe
1               5
```

```
<210> SEQ ID NO 62
<211> LENGTH: 5
<212> TYPE: PRT
<213> ORGANISM: Artificial
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (1)..(1)
<223> OTHER INFORMATION: Aib
<220> FEATURE:
<221> NAME/KEY: MOD_RES
<222> LOCATION: (3)..(3)
<223> OTHER INFORMATION: Aib
<220> FEATURE:
<221> NAME/KEY: MOD_RES
<222> LOCATION: (5)..(5)
<223> OTHER INFORMATION: alpha(Me)Phe
<220> FEATURE:
<221> NAME/KEY: MOD_RES
<222> LOCATION: (5)..(5)
<223> OTHER INFORMATION: AMIDATION

<400> SEQUENCE: 62

Xaa Arg Xaa Arg Xaa
1               5

<210> SEQ ID NO 63
<211> LENGTH: 5
<212> TYPE: PRT
<213> ORGANISM: Artificial
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (1)..(1)
<223> OTHER INFORMATION: Aib
<220> FEATURE:
<221> NAME/KEY: MOD_RES
<222> LOCATION: (2)..(2)
<223> OTHER INFORMATION: N(Me)Arg
<220> FEATURE:
<221> NAME/KEY: MOD_RES
<222> LOCATION: (3)..(3)
<223> OTHER INFORMATION: Aib
<220> FEATURE:
<221> NAME/KEY: MOD_RES
<222> LOCATION: (5)..(5)
<223> OTHER INFORMATION: alpha(Me)Phe
<220> FEATURE:
<221> NAME/KEY: MOD_RES
<222> LOCATION: (5)..(5)
<223> OTHER INFORMATION: AMIDATION

<400> SEQUENCE: 63

Xaa Xaa Xaa Arg Xaa
1               5

<210> SEQ ID NO 64
<211> LENGTH: 5
<212> TYPE: PRT
<213> ORGANISM: Artificial
<220> FEATURE:
<223> OTHER INFORMATION: synthetic peptide
<220> FEATURE:
<221> NAME/KEY: MOD_RES
<222> LOCATION: (1)..(1)
```

```
<223> OTHER INFORMATION: ACETYLATION
<220> FEATURE:
<221> NAME/KEY: MOD_RES
<222> LOCATION: (1)..(1)
<223> OTHER INFORMATION: Aib
<220> FEATURE:
<221> NAME/KEY: MOD_RES
<222> LOCATION: (2)..(2)
<223> OTHER INFORMATION: N(Me)Arg
<220> FEATURE:
<221> NAME/KEY: MOD_RES
<222> LOCATION: (3)..(3)
<223> OTHER INFORMATION: Aib
<220> FEATURE:
<221> NAME/KEY: MOD_RES
<222> LOCATION: (4)..(4)
<223> OTHER INFORMATION: N(Me)Arg
<220> FEATURE:
<221> NAME/KEY: MOD_RES
<222> LOCATION: (5)..(5)
<223> OTHER INFORMATION: alpha(Me)Phe
<220> FEATURE:
<221> NAME/KEY: MOD_RES
<222> LOCATION: (5)..(5)
<223> OTHER INFORMATION: AMIDATION

<400> SEQUENCE: 64

Xaa Xaa Xaa Xaa Xaa
1               5

<210> SEQ ID NO 65
<211> LENGTH: 5
<212> TYPE: PRT
<213> ORGANISM: Artificial
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (1)..(1)
<223> OTHER INFORMATION: Aib
<220> FEATURE:
<221> NAME/KEY: MOD_RES
<222> LOCATION: (3)..(3)
<223> OTHER INFORMATION: Aib
<220> FEATURE:
<221> NAME/KEY: MOD_RES
<222> LOCATION: (4)..(4)
<223> OTHER INFORMATION: N(Me)Arg
<220> FEATURE:
<221> NAME/KEY: MOD_RES
<222> LOCATION: (5)..(5)
<223> OTHER INFORMATION: alpha(Me)Phe
<220> FEATURE:
<221> NAME/KEY: MOD_RES
<222> LOCATION: (5)..(5)
<223> OTHER INFORMATION: AMIDATION

<400> SEQUENCE: 65

Xaa Arg Xaa Xaa Xaa
1               5

<210> SEQ ID NO 66
<211> LENGTH: 4
<212> TYPE: PRT
<213> ORGANISM: Artificial
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: ACETYLATION
<220> FEATURE:
```

```
<221> NAME/KEY: MOD_RES
<222> LOCATION: (4)..(4)
<223> OTHER INFORMATION: AMIDATION

<400> SEQUENCE: 66

Arg Glu Arg Phe
1

<210> SEQ ID NO 67
<211> LENGTH: 5
<212> TYPE: PRT
<213> ORGANISM: Artificial
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: x is pGlu

<400> SEQUENCE: 67

Xaa Arg Glu Arg Tyr
1               5

<210> SEQ ID NO 68
<211> LENGTH: 6
<212> TYPE: PRT
<213> ORGANISM: Artificial
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: FORMYLATION
<220> FEATURE:
<221> NAME/KEY: MOD_RES
<222> LOCATION: (1)..(1)
<223> OTHER INFORMATION: x is Nle
<220> FEATURE:
<221> NAME/KEY: MOD_RES
<222> LOCATION: (4)..(4)
<223> OTHER INFORMATION: x is Nle

<400> SEQUENCE: 68

Xaa Leu Phe Xaa Tyr Lys
1               5
```